(12) United States Patent
Chapman et al.

(10) Patent No.: US 9,101,925 B2
(45) Date of Patent: Aug. 11, 2015

(54) CENTRIFUGE AND SEPARATION VESSEL THEREFORE

(75) Inventors: John R. Chapman, Sacramento, CA (US); Rodney Sparks, Antelope, CA (US); Philip H. Coelho, Sacramento, CA (US)

(73) Assignee: MicroAire Surgical Instruments, LLC, Charlottesville, VA (US)

( * ) Notice: Subject to any disclaimer, the term of this patent is extended or adjusted under 35 U.S.C. 154(b) by 989 days.

(21) Appl. No.: 13/199,111

(22) Filed: Aug. 19, 2011

(65) Prior Publication Data

US 2012/0065047 A1    Mar. 15, 2012

Related U.S. Application Data

(60) Provisional application No. 61/401,877, filed on Aug. 21, 2010.

(51) Int. Cl.
*B01L 3/00* (2006.01)
*G01N 33/49* (2006.01)
*A61M 1/36* (2006.01)

(52) U.S. Cl.
CPC ............ *B01L 3/5021* (2013.01); *A61M 1/3693* (2013.01); *G01N 33/491* (2013.01); *B01L 2300/0851* (2013.01); *B01L 2400/0409* (2013.01)

(58) Field of Classification Search
CPC . G01N 33/491; A61M 1/3693; B01L 3/5021; B01L 2300/0851; B01L 2400/0409
USPC .......... 422/533, 548, 559; 494/16, 22, 31, 33, 494/34
See application file for complete search history.

(56) References Cited

U.S. PATENT DOCUMENTS

| | | | |
|---|---|---|---|
| 6,544,162 B1 | 4/2003 | Van Wie et al. | |
| 2006/0175242 A1* | 8/2006 | Dorian et al. | 494/36 |
| 2010/0163493 A1* | 7/2010 | Hein et al. | 210/695 |

* cited by examiner

*Primary Examiner* — Timothy Cleveland
(74) *Attorney, Agent, or Firm* — Bret E. Field; Khin K. Chin; Bozicevic, Field & Francis LLP

(57) ABSTRACT

The centrifugation vessel includes an outer wall containing an interior space. A dam defines a barrier which divides the interior space into at least two regions including a catch basin defining a higher gee region and a reservoir defining a lower gee region. These regions are joined together over the dam. The dam includes a face which is preferably tapered to enable optimization of speed of separation of a sample placed within the vessel. The vessel is usable in a biological sample processing method by having the higher gee region of the vessel configured to have an elongate form and the volume optimized for collection of a higher density fraction of the sample. Supply and withdrawal tubes extend into the regions for reliable extraction and separate collection of differing density fractions after separation by centrifugation.

6 Claims, 7 Drawing Sheets

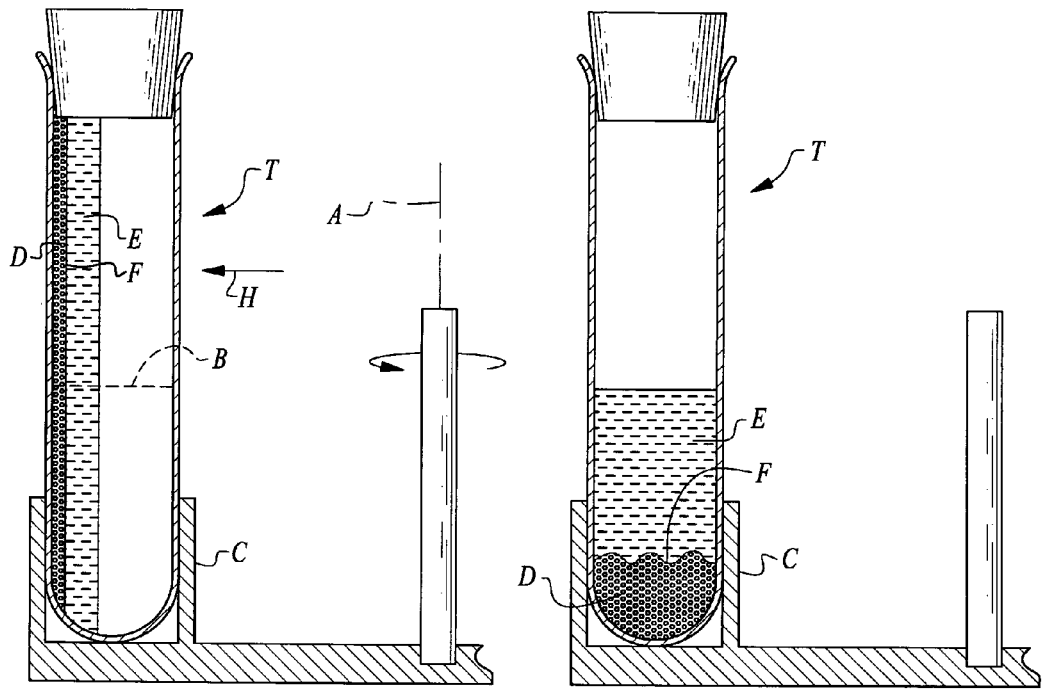
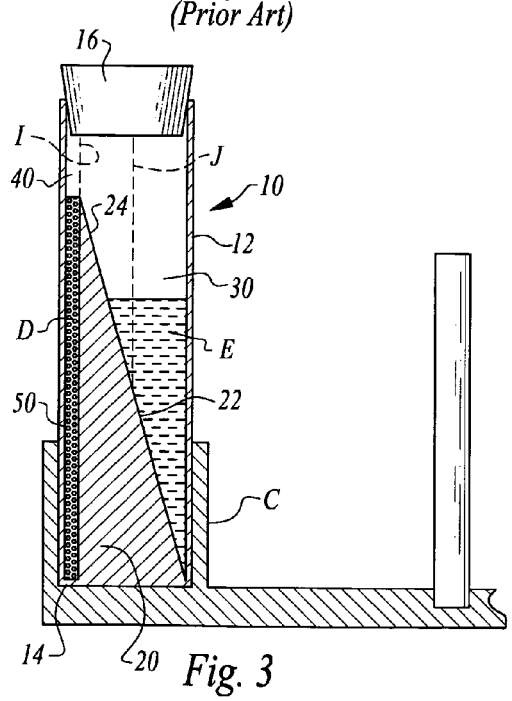
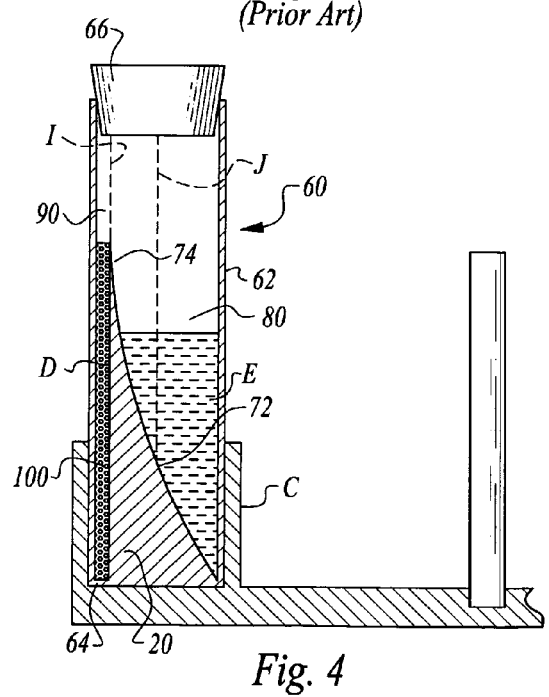
Fig. 1 (Prior Art)
Fig. 2 (Prior Art)
Fig. 3
Fig. 4

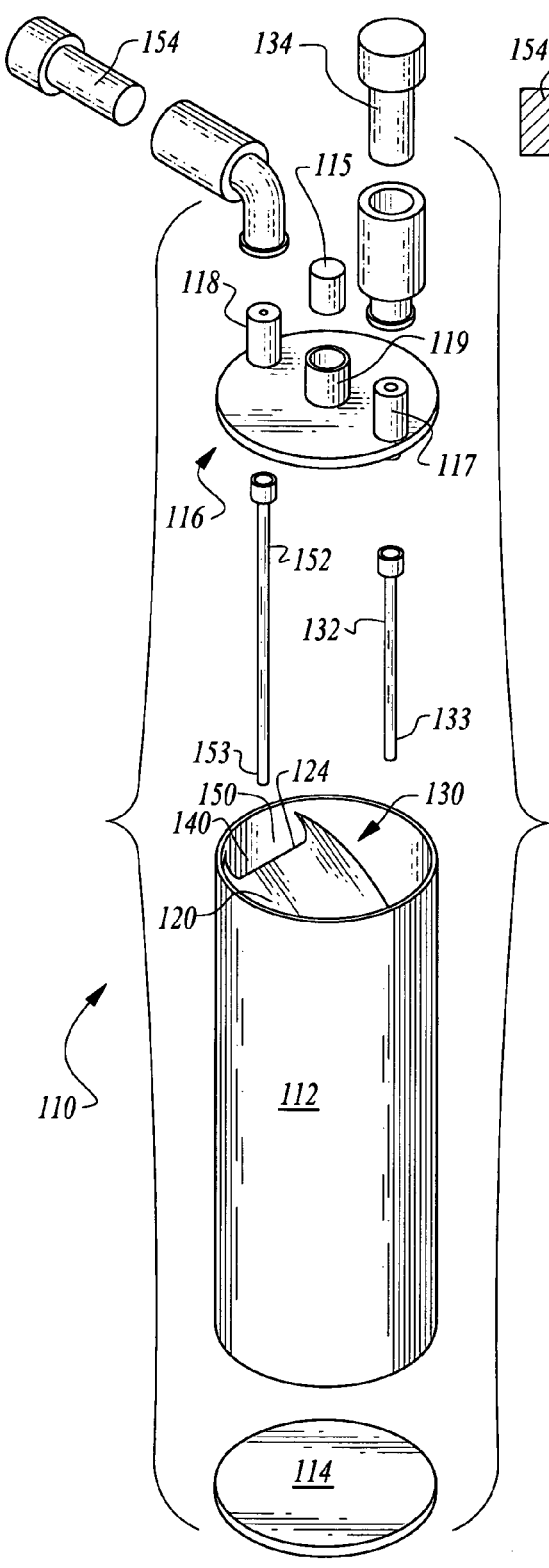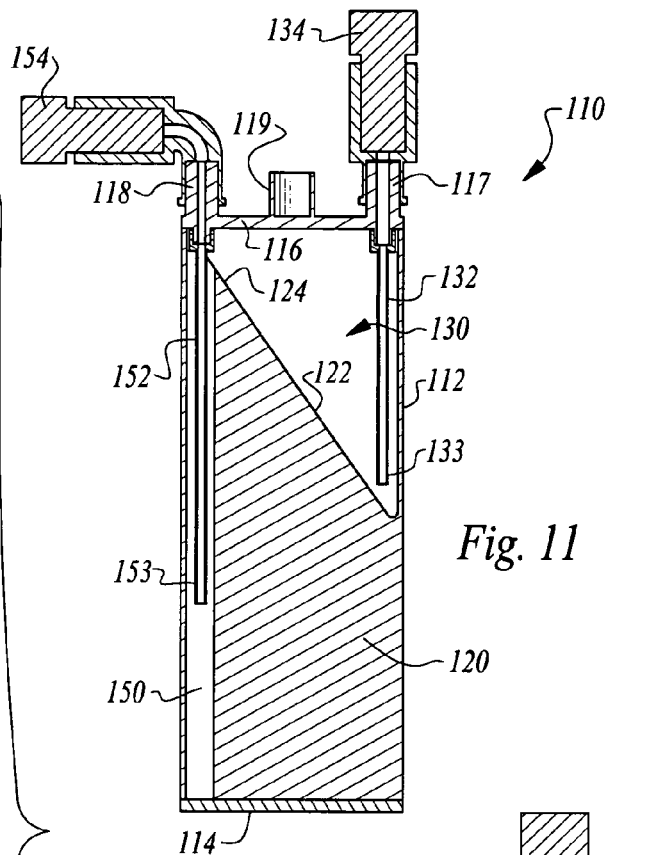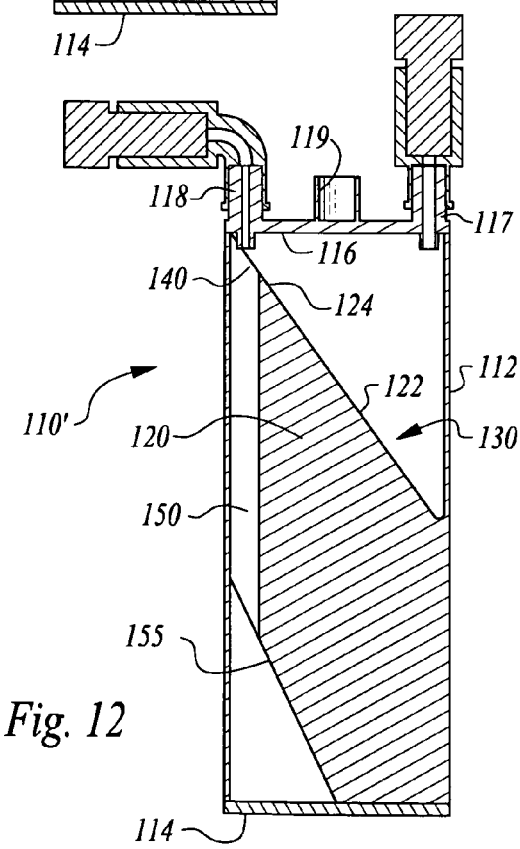
Fig. 10
Fig. 11
Fig. 12

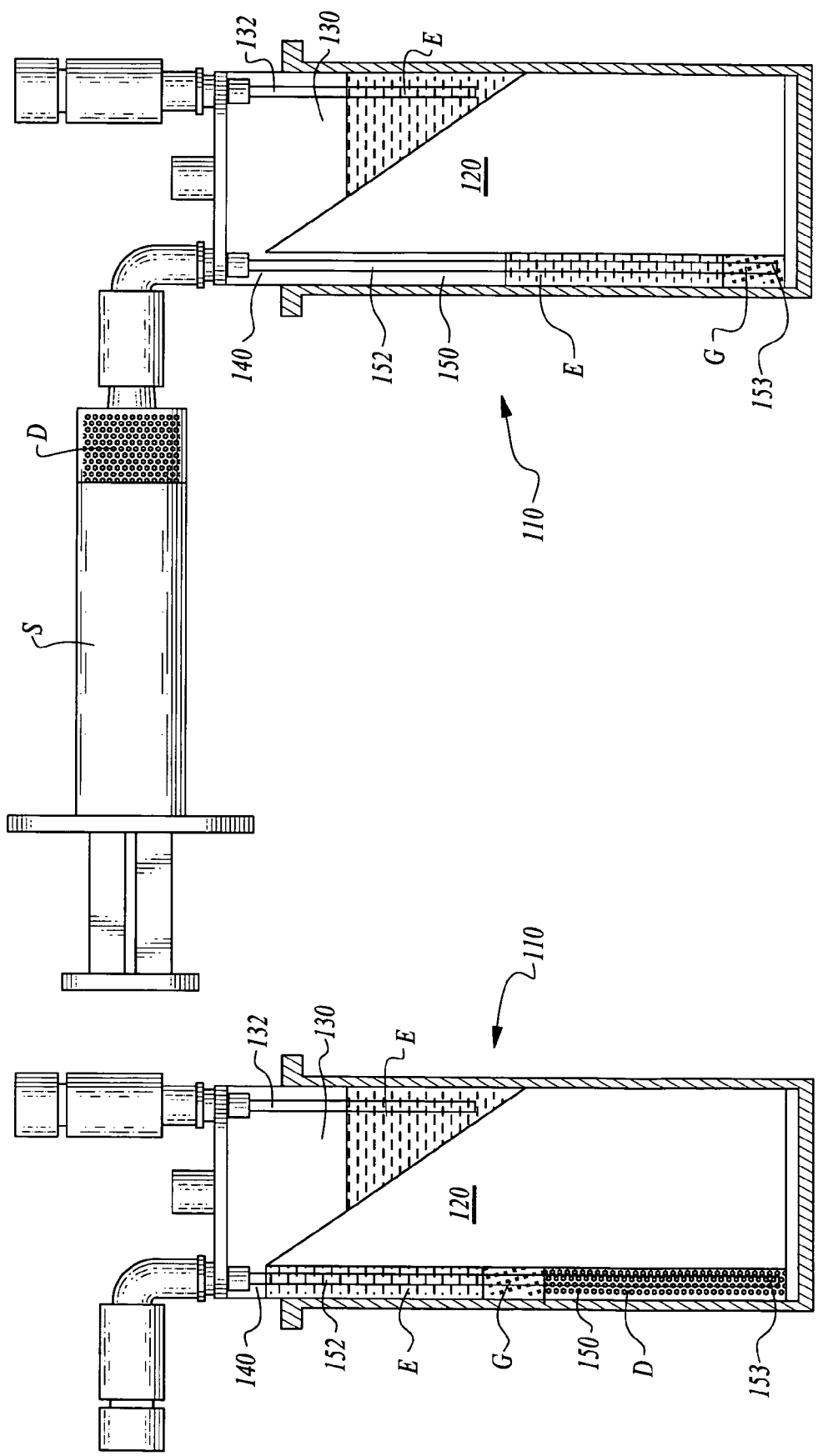

CENTRIFUGE AND SEPARATION VESSEL THEREFORE

CROSS-REFERENCE TO RELATED APPLICATIONS

This application claims benefit under Title 35, United States Code §119(e) of U.S. Provisional Application No. 61/401,877 filed on Aug. 21, 2010.

FIELD OF THE INVENTION

The following invention relates to centrifuges and vessels therefore which are used in processes for separating a sample into fractions of different densities. More particularly, this invention relates to centrifuges and centrifuge operation methods which utilize sample containing vessel geometry to speed the sample separation process and maintain separation after centrifugation.

BACKGROUND OF THE INVENTION

Essentially a centrifuge is an apparatus that separates particles that are in a fluid. Centrifugation provides a means for achieving two goals through one approach: particles can be both concentrated and purified under centrifugal forces. Centrifugation of particles in a suspending medium causes the particles to sediment rapidly in the direction outward from the center of rotation. The centrifugal force generated by centrifugation is proportional to the speed of rotation and the radius of the rotor. At a fixed centrifugal force and medium viscosity, the sedimentation rate of the particle is proportional to the molecular weight of the particle and the difference between its density and the density of the medium. There are two types of centrifugation procedures: one is "preparative" which is used to isolate specific particles; the other is called "analytical" which is used to measure the physical properties of sedimenting particles. When a suspension is rotated at a certain speed or revolutions per minute (RPM), centrifugal force causes the particles to move radially away from the axis of rotation.

Centrifuges are among a select group of laboratory instruments that are as scalable as they are configurable. Individuals who have used bench top centrifuges that handle sub-milliliter volumes may be surprised to learn that centrifuges, some as large as rooms, are used in industrial processing. The use of centrifuges has been summarized in the following books, the entire contents are incorporated herein: *Centrifugal Separations in Biotechnology* by Wallace Woon-Fong Leung Academic Press; 1 edition (Aug. 30, 2007) (by reference and for industrial applications reviewed in *Perry's Chemical Engineers' Handbook 8/E Section 18:Liquid-Solid Operations and Equipment* McGraw-Hill Professional (Aug. 1, 2007); *Industrial Centrifugation Technology* by Wallace Woon-Fong Leung (Feb. 1, 1998); *Biological Centrifugation (The Basics)* by J. M. Graham (Oct. 15, 2001); *Refining iron-contaminated zinc by filtration and centrifugation* by John A. Ruppert (Jan. 1, 1967); *Processing by Centrifugation* by Liya L. Regel and William R. Wilcox (Sep. 1, 2001); *Centrifugation in Density Gradients* by C. A. Price (October 1982); *Decanter Centrifuge Handbook* by A. Records and K Sutherland (Mar. 16, 2001); *Bioseparations Science and Engineering (Topics in Chemical Engineering* (Oxford University Press) by Roger G. Harrison, Paul W. Todd, Scott R. Rudge, and Demetri Petrides (Oct. 31, 2002).

Centrifuge designs are simple, consisting of an enclosed compartment inside which a rotor spins rapidly. Rotors, which can usually be interchanged, contain equally spaced openings into which sample tubes are inserted. Samples will either spin at a fixed angle relative to the rotating axis or "swing out" to perpendicular under centripetal force as the rotor speed increases. Forces generated as the rotor spins cause components in the sample to migrate toward the bottom of the sample tube, according to weight or density.

Entry-level mini-centrifuges easily fit on a bench top, operate at a single, relatively low speed, generate low gravitational (g) forces, and cost only a few hundred dollars. "Minis" are used for samples whose components are easily separated by density. Most medical and veterinary office centrifuges are of this type. The next level up, compact bench top centrifuges, spin tubes of up to about 2 mL and create tens of thousands of gs. Researchers use them to separate DNA, proteins, and cellular components.

There are many ways to differentiate centrifuges by type, speed, and features. Beckman-Coulter (Fullerton, Calif.), for example, divides its product line into three basic platforms: bench top devices operating at up to about 10,000 rpm, "washing machine" centrifuges that provide up to about 100,000 g, and ultracentrifuges that deliver in excess of one million g. In fact, one could argue that all centrifuges exist along a continuum of features that may be mixed and matched, which include g-force generated, sample tube size, refrigeration capabilities, rotation angle, computerization, and others. The ultracentrifuge is a centrifuge optimized for spinning a rotor at very high speeds, capable of generating acceleration as high as 1,000,000 g (9,800 km/s$^2$). There are two kinds of ultracentrifuges, the preparative and the analytical ultracentrifuge. Both classes of instruments find important uses in molecular biology, biochemistry and polymer science.

Common Centrifugation Vocabulary and Formulas.
Pellet: hard-packed concentration of particles in a tube or rotor after centrifugation.
Supernatant: The clarified liquid above the pellet.
Adapter: A device used to fit smaller tubes or centrifugal devices in the rotor cavities.
RPM: Revolutions Per Minute (Speed).
$R_{max}$: Maximum radius from the axis of rotation in centimeters.
$R_{min}$: Minimum radius from the axis of rotation in centimeters.
99999: Relative centrifugal Force. RCF=11.17×Rmax (RPM/1000)$^2$
K-factor: Pelleting efficiency of a rotor. Smaller the K-factor, better the pelleting efficiency.

$$K = \frac{2.53 \times 10^{11} \text{Ln}(R_{max}/R_{min})}{(RPM)^2}$$

S-value: the sedimentation coefficient is a number that gives information about the molecular weight and shape of the particle. S-value is expressed in Svedberg units. The larger the S-value, the faster the particle separates.

The force on the particles (compared to gravity) is called Relative Centrifugal Force (RCF). For example, an RCF of 500×g indicates that the centrifugal force applied is 500 times greater than Earth's gravitational force. Modern day ultracentrifuges can generate forces in excess of 300,000 times that of gravity, forces sufficient to overcome the very cohesion of most molecules (including the metal of the rotor). The force is usually given as some value times that of gravity (g) and is called RCF. The centrifugal force is dependent upon the radius of the rotation of the rotor, the speed at which it rotates, and the design of the rotor itself (fixed angle, vs swinging bucket). Rotor speed and design can be held constant, but the radius will vary from the top of a centrifuge tube to the bottom. If a measurement for the radius is taken as the midpoint, or as an average radius, and all forces are mathematically related to gravity, then one obtains a relative centrifugal force, labeled as xg. Centrifugation procedures are given as xg measures, since RPM and other parameters will vary with the particular instrument and rotor used. Relative Centrifugal Force is a constant that is independent of the apparatus used.

Protocols for centrifugation typically specify the amount of acceleration to be applied to the sample, rather than specifying a rotational speed such as revolutions per minute. This distinction is important because two rotors with different diameters running at the same rotational speed will subject samples to different accelerations. During circular motion the acceleration is the product of the radius and the square of the angular velocity and it is traditionally named "relative centrifugal force" (RCF). The acceleration is measured in multiples of "g" (or x"g"), the standard acceleration due to gravity at the Earth's surface, and it is given by $$RCF = \frac{r(2\pi N)^2}{g}$$

where
g is earth's gravitational acceleration,
r is the rotational radius,
N is the rotational speed, measured in revolutions per unit of time.
This relationship may be written as $$RCF = 1.118 \times 10^{-5} r_{cm} N_{RPM}^2$$

where
$r_{cm}$ is the rotational radius measured in centimeters (cm),
$N_{RPM}$ is rotational speed measured in revolutions per minute (RPM).

In 1851, George Gabriel Stokes derived an expression, now known as Stokes' law, for the frictional force, also called drag force, exerted on spherical objects with very small Reynolds numbers (e.g., very small particles) in a continuous viscous fluid. Stokes' law is derived by solving the Stokes flow limit for small Reynolds numbers of the generally unsolvable Navier-Stokes equations:

$$F_d = 6\pi\mu RV$$

where:
$F_d$ is the frictional force acting on the interface between the fluid and the particle (in N),
μ is the fluid's viscosity (in [kg m$^{-1}$ s$^{-1}$]),
R is the radius of the spherical object (in m), and
V is the particle's velocity (in m/s).

If the particles are falling in the viscous fluid by their own weight due to gravity, then a terminal velocity, also known as the settling velocity, is reached when this frictional force combined with the buoyant force exactly balance the gravitational force. The resulting settling velocity (or terminal velocity) is given by:

$$V_s = \frac{2}{9} \frac{(\rho_p - \rho_f)}{\mu} g R^2$$

where:
$V_s$ is the particles' settling velocity (m/s) (vertically downwards if $\varrho_p > \varrho_f$, upwards if $\varrho_p < \varrho_f$),
g is the gravitational acceleration (m/s$^2$),
$\varrho_p$ is the mass density of the particles (kg/m$^3$), and
$\varrho_f$ is the mass density of the fluid (kg/m$^3$).

From application of Stoke Law, the following principles are derived: The sedimentation rate of particles is proportional to their size; the sedimentation rate is proportional to the density of the particle and to the medium; the sedimentation rate is null when both densities are the same; the sedimentation rate diminishes by increasing the viscosity of the medium, and the sedimentation rate increases by increasing the force field.

Separation Methods.

Centrifugal separations can be separated into two basic types: differential pelleting and zonal separations. Differential pelleting is most useful for crude separations of raw material where purity and yield are not critical. The method involves sedimenting particles out of solution, and either retaining the pellet or supernatant depending on where the material of interest is located. As predicted by the equations above, larger particles will sediment prior to smaller ones, and more dense particles prior to less dense ones. In addition, asymmetrical particles will sediment more slowly than spherical ones of the same mass and density. The separations are not clean, however, since the centrifugal force required to pellet large particles from the top of a sample will also pellet small particles from the bottom. The greater the difference in sedimentation rate between the particles being separated, the cleaner the preparation will be.

Differential Centrifugation.

In this method, the centrifuge tube is filled with an uniform fluid mixture. After centrifugation are obtained two fractions: a pellet that contains the sedimented material and a supernatant with the material not sedimented. The method is nonspecific, and it is difficult to assure if the desired particle will remain in the supernatant, in the pellet or distributed between both; but is a very useful technique. An example of the application is the the elimination of prokaryotic cells in culture broths. Centrifugation of cultures to 10.000xg for 20 minutes is enough to create the required centrifugal force necessary to sediment bacteria cells.

Protein Precipitation with Ammonium Sulfate.

The saline precipitation is a technique used in the initial steps of enzyme purification and in some immunoassays. Proteins are surface polyelectrolytes, when a salt is added to the medium, their ions neutralize the protein charges, arriving at a situation in which there aren't net charge, then, proteins flocculate. This technique requires differential centrifugation: centrifuge to 10,000xg for 60 minutes so that the proteins that are flocculating are precipitated.

Thermal Treatment.

Some proteins are more thermostable than others which can be used as a method for isolating and concentrating. The denatured proteins tend to become aggregated and by using differential centrifugation can be eliminated by their sedimentation.

Zonal Separations.

There are two types of zonal separations, both of which rely on density gradients: rate zonal and isopycnic. Rate-zonal centrifugation separates particles based on differences in their sedimentation coefficients (s), which is a function of both particle size and density. In practice, differences in size dominate the differences in sedimentation velocity (s) among most biological particles, since the range of densities is not large and s varies as the square of particle diameter. Isopycnic separations discriminate among particles based solely on differences in buoyant density. In both techniques, centrifugation is carried out in a density gradient, which, among other functions, prevents mixing of the sample thereby ensuring that separated particles remain separated.

For rate zonal separations, a sample is introduced to the top of a density gradient. When subjected to centrifugal force, the sample components migrate through the gradient according to their s. Particles migrate at different speeds, resulting in greater distance between particles having different s over time. Because the particles do not come to rest at equilibrium in the gradient, care must be taken so that the particles of interest do not pellet. For effective separations, the initial sample volume should be small (the sample layer should be only a few millimeters thick), because the sample zone continues to widen over time as a result of diffusion. Therefore, while rate zonal gradients eliminate problems associated with pelleting during the purification, a suitable concentration step that does not result in pelleting or aggregation must be employed prior to using this technique. Many different types of density gradient media may be employed for rate zonal separations. Choosing the appropriate medium requires matching the properties of the medium to one's specific application. In general, it is beneficial to employ media preparations of high viscosity for rate zonal separations because viscous forces will magnify differences in settling velocity between similar particles.

In isopycnic (or equilibrium buoyant density) separations, particles migrate through the density gradient until they reach the point at which their density is equal to that of the surrounding medium. Media used for this type of separation must therefore be able to form a solution that is at least as dense as the particle that are to be purified. Samples may be top-loaded or bottom-loaded in preformed density gradients, or homogeneously mixed with a self-forming gradient medium before centrifugation. As particles approach their equilibrium position in a gradient, the difference in density between the particle and the medium decreases and, consequently, so does the migration rate of the particle. Particles become increasingly focused over time until the focusing force is balanced by diffusion. Achieving equilibrium, at which point the particles are most focused, can require long centrifugation runs under high g-forces. This method eliminates pelleting and aggregation concentrated and purified target particle preparations at the same time. Isopycnic separations also provide a means for directly determining buoyant density, a commonly reported physico-chemical property of materials.

Because the two zonal techniques described above separate based on partially independent properties (size versus density), they can be used sequentially to separate particles that may not be separable by either method alone. Two-dimensional separations have been particularly valuable for biological particulate purification, since most biological particulates have a combination of sedimentation coefficient and buoyant density that distinguishes them from other fluid constituents.

Density Gradient Centrifugation.

Density gradient centrifugation is a popular method for fractionation of nucleic acids, virus particles and proteins. This is done by centrifugation of a mixture of particles or components in a density gradient column. Particles or components with different densities will be separated at different positions in the density gradient column. Basically, there are two types of density gradient centrifugation, termed rate zonal and isopycnic. Preparation of density gradients. In either zonal or isopycnic density gradient centrifugation, a density gradient has to be prepared prior to centrifugation by either a hand-layering process or by employing a density gradient former. A number of materials such as sucrose, Ficoll, or salts such as NaCl, NaBr, or CsCl, can be used for preparation of the density gradient. A sucrose density gradient can be prepared by pipetting into a centrifuge tube layers of progressively lower concentrations of sucrose on top of higher concentrations. Density gradient columns can also be prepared by the use of a syringe with a piece of tubing attached to the syringe needle (20-22 gauge). To prepare a 5-20% sucrose density gradient in a 15 ml tube, start by placing 3 ml of 5% sucrose in the tube and then carefully inject the 3 ml of 10% sucrose into the tube by keeping the tip of the syringe tubing at the bottom of the centrifuge tube. Repeat the process with 3 ml of 15% and 3 ml of 20% sucrose. When the preparation is completed, remove the syringe tubing carefully by holding the tip of tubing against the wall of the centrifuge tube. Ficoll and cesium chloride density gradients can be prepared in a similar manner. Density gradients thus prepared can either be used immediately as a step gradient or made into a linear gradient by allowing it to diffuse in a refrigerator overnight.

Rate Zonal Density Gradient Centrifugation.

In rate zonal density gradient centrifugation, a sample solution containing particles to be fractionated is layered on top of the density gradient column. Under centrifugation the particles will start to sediment through the density gradient into separate zones. Each zone consists of particles with the same sedimentation rate. In the rate zonal centrifugation, centrifugation must be terminated before any of the separated zones reach the bottom of the tube, since the density of some zones may be higher than the highest density area in the density gradient.

Isopycnic (="same density") density gradient centrifugation. In isopycnic density gradient centrifugation, the density gradient column encompasses the whole range of densities of sample particles. Each particle will sediment only to the position in the gradient where the density in the gradient column equals its own density, and the particle will remain at this position. In the isopycnic method, it is not always convenient to form a gradient artificially and layer the sample on top of the gradient column. It is sometimes necessary to start with a uniformly-mixed solution of gradient material and sample. During centrifugation, gradient material redistributes in the tube and forms a linear density gradient. At the same time, sample particles which are initially distributed throughout the tube either sediment or float to their isopycnic positions. This type of procedure is termed the self-generating gradient technique.

Historically, self-generating isopycnic density gradient centrifugation have generally required long hours of centrifugation. For example, isopycnic "banding" of DNA can take 36-48 hours in a self-generating cesium chloride density gradient using standard swinging-bucket or fixed-angle ultracentrifuge rotors. The running time cannot be shortened by increasing the rotor speed, since this only results in changing the positions of zones in the tube due to the redistribution of gradient material further down the tube. Run times can be decreased by shortening the distance over which the gradient forms, however. A recent innovation to decrease running times for DNA preparation (down to 3-4 hours) has been the use of "vertical" or "near-vertical" rotors, in which the gradient forms across the diameter, rather than the length of the tube.

Separated zones ("bands") from both rate zonal and isopycnic density gradient centrifugation can be removed by: (i) puncturing a hole on the bottom of the tube and collecting the fractions or drops either manually or using a fraction collector, (ii) removing successive zones from the top of the unpunctured tube, or (iii) puncturing the tube through the side to recover a band as a single fraction.

Application of Density Gradient Centrifugation.

Density gradient centrifugation has been used extensively in separation and purification of a wide variety of biological materials. It is particularly well suited for the study of viruses and nucleic acids. Cells and sub-cellular components such as bacteria, nucleoids, ribosomes, membranes, etc. have been isolated and purified with this technique.

Numerous investigators have identified the criteria for choosing density gradient media for biological separations (Cline and Ryel 1971; Hinton et al. 1974). In summary, the criteria are as follows: The media should be inert or at least nontoxic to the specimen (minimal osmotic effect, ionic strength, and neutral pH); the media should form a solution covering the density range for the particular application, and be stable in solution; the physical and chemical properties of the media should be known, and it be possible to use one or more properties to determine the precise concentration of the media; the solution should not interfere with monitoring of zones of fractionated material within the gradient; it should be easy to separate the sample from gradient material without loss of the sample or its activity; and the gradient media should be available as a pure compound; and be relatively inexpensive.

Ionic Media.

Alkali metal salts, such as cesium chloride, are most widely used for making isopycnic gradients with any standard technique including preformed or self-forming gradients. Metal salts can provide some of the densest preparations available, have a low viscosity, and their concentration in solution is easily measured by refractive index. The major drawbacks of alkali metals lie in their effects on biological activity; salt solutions have high ionic strengths, which disrupt protein-protein and nucleic acid-protein bonds, and have high osmolarities, affecting particle hydration.

Small hydrophilic organic molecules (sucrose, glycerol, sorbitol, etc.) that non-ionic media. Sucrose meets most of the criteria of an ideal medium for rate zonal separations, being biologically inert, stable, and relatively cheap. Due to its popularity as such, sucrose is very well characterized with respect to concentration, viscosity, density, and refractive index, making it easy to develop and adapt methods for uncharacterized particulates. While sucrose has little effect on intermolecular bonding and is non-ionic, high osmotic pressure may cause shrinkage in enveloped viruses and thereby affect infectivity in sensitive viruses. The high viscosity of sucrose at concentrations useful for virus separations may aid in separation between similarly sized particles under rate zonal conditions, but the high viscosity and relatively low density limits the application of sucrose and other small organic molecules in isopycnic separations of viruses. Other sugars, notably glycerol and sorbitol, have also been used effectively as rate zonal media. These gradients need to be preformed as solutions of small organic molecules do not generally form gradients when centrifuged.

High molecular-weight organics (Ficoll, dextran, glycogen, etc.). High molecular-weight polysaccharides do not penetrate intact biological membranes and have a lower osmolarity than solutions of monosaccharides. Therefore, these media may be especially useful when employed with biological particles. Unfortunately, due to the size of these polysaccharides, they cannot be removed from the sample by dialysis or ultrafiltration, so dilution and high-speed centrifugation are generally required, which are contraindicated with sensitive specimens as discussed above. Since polysaccharide media such as Ficoll (GE Healthcare) and dextran diffuse slowly, it is necessary to preform linear gradients using gradient mixers. This characteristic also ensures that gradients are quite stable once formed. The high viscosity of these media necessitates longer spin times than those of sucrose gradients.

Colloidal Silica (Percoll, Ludox, etc.). Colloidal silica suspensions such as Percoll (GE Healthcare) and Ludox (DuPont) are truly non-ionic media that can be used to rapidly generate self-forming gradients. These media are well characterized, permitting the use of refractive index for examining density profiles of gradients since absorption prohibits monitoring by UV light. Percoll density marker bead kits, available from a number of vendors (e.g., Sigma-Aldrich, product DMB-10), are useful for visually monitoring gradient profiles. Whereas colloidal media cannot be effectively filter sterilized, they may be autoclaved before being adjusted for osmolarity and can be used over a wide pH range (5.5-10 for Percoll). Percoll is commonly used for cell separations, because the suspension of colloidal silica can be prepared in almost any buffer required to maintain cell viability. Another limitation is that the silica particles may begin to pellet before smaller viruses have time to form discrete, purified bands. To remove Percoll from virus purifications requires dilution and high-speed differential centrifugation (i.e., 100,000 g for 2 h in a swinging bucket or 1.5 h in an angled rotor), which may lead to aggregation and deactivation of viruses, as previously discussed.

Iodinated organic compounds (Nycodenz, OptiPrep, and metrizamide). Iodinated compounds provide an excellent combination of biological inertness, a wide density range, and low viscosity, which allows for reduced spin times. These compounds, including Nycodenz (Axis-Shield), iodixanol (sold as OptiPrep by Axis-Shield), and metrizamide, are heat stable, autoclavable, and of minimal ionic strength.

In U.S. Pat. No. 5,605,529 entitled "HIGH EFFICIENCY CENTRIFUGE ROTOR" issued on Feb. 25, 1997 to Petithory, the entire contents are incorporated herein by reference, disclosed about the uses of fixed angular rotors in centrifuges. The field of the Petithory invention was relating generally to centrifuge rotors, and more particularly to fixed angle centrifuge rotors.

Most blood chemistry tests require preparation of serum or plasma prior to analysis. To this end, red blood cells and other cellular material are separated from the patient's blood following collection. Typically, blood is collected in evacuated tubes and centrifuged at 2000-3000 rpm for 10-20 15 minutes.

One type of centrifuge rotor which houses tubes for centrifugation is a fixed angle rotor, in which the tubes are retained in cavities angled relative to the axis of rotation. The dynamics of fixed angle rotors and their ability to enhance the speed of centrifugation are known in the art. The clearing efficiency (K-factor) of fixed angle rotors, which corresponds to the time required to sediment a specific particle in a known medium at a given speed of rotation, can be calculated using the following formula:

$$K\text{-factor} = \frac{2.53 \times 10^{11} \times Ln\left(\frac{r_1}{r_2}\right)}{N^2}$$

where $r_1$=radius, in cm, from the outermost point of liquid in the tube to the central axis of rotation, $r_2$ radius, in cm, from the center of the top of liquid within the tube to the central axis of rotation and N=rpm.

It is apparent from the above formula that a rotor having tube cavities inclined at a steep angle (approaching 0° in reference to the axis of rotation) can provide the lowest K-factor, and the greatest separation efficiency. However, there are drawbacks associated with using a rotor having steeply angled tube cavities including the fact that the steeper the angle, the greater the tendency of particles to adhere to the outermost wall of the tube, which could lead to contamination of the supernatant.

Another drawback is that the sedimentation boundary formed in a fixed angle rotor centrifuge device is significantly larger than the sedimentation boundary formed in centrifuges using a swing-out style rotor.

Another disadvantage of a steeply angled rotor occurs when gel barrier tubes are used. The position of the gel band along the top side-wall of the processed tube makes it difficult to pipette the supernatant plasma or serum without coming into contact with the gel material. This is especially important in analyzers which employ primary tube sampling capability. Since the thickness of the gel band decreases with the relative steepness of the tube angle, the band can collapse upon deceleration and cause contamination of the supernatant with the particles in the gel.

Still another disadvantage is that there exists a "mixing effect" during reorientation of the tubes from the horizontal position to the vertical position during deceleration, which also increases with the steepness of the tubes within the rotor. During sedimentation, particles travel outward from the axis of rotation until they hit the wall of the tube, then slide downward along the tube wall. This descending layer of increased particle concentration combined with a corresponding ascending layer of reduced concentration fluid creates a fluid flow within the tube which increases the time required to sediment particles, particularly those of low density or irregular shape.

A final disadvantage of using steeply angled tube cavity rotors is that as the steepness of the tube increases, the capacity of the tube decreases. Since the closure of these tubes can trap particles, there is a limit to the tube angle that can be used during centrifugation.

Advances in the speed of test instrumentation have created a demand for faster blood separation methods, and particularly for high speed separation of the blood or serum within the original blood collection tube while maintaining a minimal distortion of the separation boundary within the sample containers.

Centrifuges are suited and used for the separation of components including cells, organelles or macromolecules contained in biologic fluids including bone marrow, peripheral blood, urine, phlegm, synovial semen, milk, saliva, mucus, sputum, exudates, cerebrospinal fluid, amniotic fluid, cord blood, intestinal fluid, cell suspensions, tissue digests, tumor cell containing cell suspensions, microbe containing cell suspensions, radiolabelled cell suspensions and cell culture fluid for therapeutic or diagnostic purposes. Centrifuges are well suited for the washing of cell suspensions and other particulate matter. Centrifuges also are used for separation of components present in aqueous solutions, lake water, ocean water, river water, waste water, and sewage for the purpose of preparative analytical testing or purification. Centrifuges are also suited for the separation of a component of an inorganic or organic chemical reaction that has resulted in the formation of a precipitate or flocculent. Centrifuges have occasionally been used for separation of particulates added to an aqueous solution for the purpose of inducing a chemical reaction and then terminating said chemical reaction by centrifugation of the heterogeneous fluid using the apparatus of the invention. Centrifuges have been used to in combination with density particles to perform immunoaffinity cell separation steps. This expansive list is still not inclusive for all the varied functions for which centrifuges are routinely employed and known in the prior art. Below are detailed examples of some of these applications.

Charlton et al. were awarded U.S. Pat. No. 4,106,907 on Aug. 15, 1978 entitled "Centrifuge Tube and Method for Performing Assay with Same", for which the entire contents are incorporated herein by reference for the purpose of handling radioactive material.

Kimura was awarded U.S. Pat. No. 4,861,477 on Aug. 29, 1989 entitled "Tubular Container for Centrifugal Separation" for which the entire contents are incorporated herein by reference. A tubular container for centrifugal separation suited for easy separation of a relatively small amount of the phase having an intermediate specific gravity from the heaviest and lightest phases. The container has a first section defining a bottom chamber of a certain volume for containing therein the heaviest phase, a second section contiguous to the first section and defining an intermediate chamber for containing therein the phase having the intermediate specific gravity, and a third section contiguous to the second section and defining an upper chamber for containing therein the lightest phase. The diameter of said second section is smaller than the diameters of the first and third sections.

Saunders et al. was awarded U.S. Pat. No. 5,422,018 on Jun. 6, 1995 entitled "Centrifuge Tube and Adaptor" for which the entire contents are incorporated herein by reference. Saunder's discloses a centrifuge tube and adaptor apparatus is provided which facilitates separation of biological materials and permits easy extraction of a fraction after centrifugation. The tube is a deformable tube with a wide upper chamber and a narrowed lower portion. The tube is supported within the centrifuge rotor or within another container within the centrifuge by a liquid support medium, which surrounds and supports the narrow portion of the tube, and thus prevents the tube from collapsing during high speed centrifugations.

Muller was awarded U.S. Pat. No. 5,260,032 on Nov. 9, 1993 entitled "Integral Centrifuge Tube and Specimen Slide" for which the entire contents are incorporated herein by reference. Muller's device was made for use in a centrifuge to automatically prepare microscope slide specimens from samples of body fluids. A centrifuge tube and specimen slide are formed integrally in a unitary device. A lens clearance section is provided as a planar surface to avoid interference between the device and the rotatable lenses of a turret microscope while the device is in viewing position on the microscope stage. The device is constructed to minimize packing of sediment and other constituent elements of the sample at the entrance to the slide member and is so configured as to admit of a step during the centrifuge process which flexes the slide member to enhance the distribution of cells deposited therein.

Levine et al. were awarded U.S. Pat. No. 5,342,790 on Aug. 30, 1994 entitled "Apparatus for Indirect Fluorescent Assay of Blood Samples" for which the entire contents are incorporated herein by reference. Levine discloses that a patient's health is diagnosed by centrifuging blood samples in a transparent tube, which tube contains one or more groups of particles such as lyposomes or plastic beads of different densities for each group. Each group of density-defined particles carries antigens or antibodies which are specific to a complement antigen or antibody which may be in the blood sample being tested, and which are indicative of the patient's health. A label tagged antibody which is specific to all bound antibody/antigen couples is added to the blood sample so as to form labeled antibody+antigen-antibody complexes (AAAC) in the blood sample. Upon centrifugation, the complexed particles will settle out in different areas in the tube according to the respective density of the particles, and the degree of label emission of the particle layers can enable qualitative or quantitative analyses of the blood sample to be made. Unbound labeled antibodies will be washed away from the complexed layers by the washing action of the descending blood cells during the centrifugation step. Unbound labeled antibodies will thus not interfere with the analysis.

Gerken was awarded U.S. Pat. No. 4,713,219 on Dec. 15, 1987 entitled "Plastic Reaction Vessel" for which the entire contents are incorporated herein by reference. Gerken describes a plastic reaction vessel for holding a small quantity of liquid comprises a vessel body which has a body flange (4) surrounding an opening formed in the body, a cover, and a connecting strip (5) which is integral with the vessel body and the cover. Opposite to the connecting strip (5), the body flange (4) has a downwardly facing abutment surface (25), which is engageable by a hooklike extension (23), which is formed on the cover (6) and extends downwardly when the cover is closed. The connecting strip (5) comprises a hinge portion (12) between its opposite end portions. The cover comprise a cylindrical skirt, which is adapted to be inserted into the vessel body through the opening therein. A sealing lip (8) is provided on the outside of said skirt at that end thereof which is adapted to be inserted into the opening of the vessel body. The cover (6) has an outwardly protruding rim (16), from which a depending flange extends, which contacts the body flange so that a parallel guidance of the cover (6) is effected in conjunction with the hinge portion of the connecting strip. An alignment of the cover (6) is effected by the sealing lip (8), which is formed on the cylindrical skirt and in sealing contact with the inside surface of the vessel body.

According to Kaiser (U.S. Published Patent Application No. 2004/0038316 A1) the improved methods of separating cells have had a great utility in the many medical and biological fields that require purified populations. Many biological techniques such as are employed in biotechnology, microbiology, clinical diagnostics and treatment, in vitro fertilization, hematology and pathology, require such processes as identification, separation, culturing, or manipulation of a target cell or particle, e.g. cell subsets, platelets, bacteria, virus particles, etc. Cell separation is a rapidly growing area of biomedical and clinical development. Improved methods of separating a desired cell subset from a complex population permit the study and use of cells that have relatively uniform and denned characteristics. Cell separation is widely used in research, e.g. to determine the effect of a drug or treatment on a targeted cell population; investigation of biological pathways; isolation of transformed or otherwise modified cell populations; etc. Present clinical uses include the isolation of hematopoietic stem cells for reconstitution of blood cells, particularly in combination with ablative chemo and radiation therapy.

The disclosure of an invention in U.S. Published Patent Application No. 2004/0182795, by Randel Dorian and Richard Storrs, the entire contents of which are hereby incorporated herein by reference, teaches an apparatus and methods for separation and concentration of plasma and plasma platelet mixtures from plasma erythrocyte mixtures such as whole blood and is particularly applicable to the preparation and use of autologous plasma concentrates.

Rapid fractionation of blood into erythrocyte, plasma or plasma-platelet fractions is desirable for the preparation of autologous concentrates from blood obtained from a patient during surgery. Each fraction can be modified or returned to the blood donor. Useful plasma fractions, with our without platelets, have value as sealants when concentrated without precipitation of fibrinogen, that is, when concentrated by removal of water therefrom in accordance with this invention. This invention has particular value for rapidly preparing autologous concentrated plasma fractions to help or speed healing, or as a hemostatic agent or tissue sealant.

Background of the Invention of U.S. Published Patent Application No. 2004/0182795, by Randel Dorian and Richard Storrs, the entire contents of which are hereby incorporated herein by reference: Blood may be fractionated and the different fractions of the blood used for different medical needs. For instance, anemia (low erythrocyte levels) may be treated with infusions of erythrocytes. Thrombocytopenia (low thrombocyte (platelet) levels) may be treated with infusions of platelet concentrate.

Under the influence of gravity or centrifugal force, blood spontaneously sediments into layers. At equilibrium the top, low-density layer is a straw-colored clear fluid called plasma. Plasma is a water solution of salts, metabolites, peptides, and many proteins ranging from small (insulin) to very large (complement components). Plasma per se has limited use in medicine but may be further fractionated to yield proteins used, for instance, to treat hemophilia (factor VIII) or as a hemostatic agent (fibrinogen).

Following sedimentation, the bottom, high-density layer is a deep red viscous fluid comprising anuclear red blood cells (erythrocytes) specialized for oxygen transport. The red color is imparted by a high concentration of chelated iron or heme that is responsible for the erythrocytes high specific gravity. Packed erythrocytes, matched for blood type, are useful for treatment of anemia caused by, e.g., bleeding. The relative volume of whole blood that consists of erythrocytes is called the hematocrit, and in normal human beings can range from about 38% to about 54%.

Depending upon the time and speed of the centrifugation, an intermediate layer can be formed which is the smallest, appearing as a thin white band on top the erythrocyte layer and below the plasma; it is called the buffy coat. The buffy coat itself generally has two major components, nucleated leukocytes (white blood cells) and anuclear smaller bodies called platelets (thrombocytes).

Leukocytes confer immunity and contribute to debris scavenging. Platelets seal ruptures in the blood vessels to stop bleeding and deliver growth and wound healing factors to the wound site. If the centrifugation is of short duration, the platelets can remain suspended in the plasma layer.

The sedimentation of the various blood cells and plasma is based on the different specific gravity of the cells and the viscosity of the medium. This may be accelerated by centrifugation according approximately to the Svedberg equation:

$$V = ((2/9)\omega^2 R (d_{cells} - d_{plasma}) r^2)/\eta_t$$

where
V=sedimentation velocity, [00111] m=angular velocity of rotation,
R=radial distance of the blood cells to the center of the rotor,
d=specific gravity,
r=radius of the blood cells, and
$\eta_t$=viscosity of the medium at a temperature of t° C.

When sedimented to equilibrium, the component with the highest specific gravity (density) eventually sediments to the bottom, and the lightest rises to the top. The rate at which the components sediment is governed roughly by the Svedberg equation; the sedimentation rate is proportional to the square of the size of the component. In other words, at first larger components such as white cells sediment much faster than smaller components such as platelets; but eventually the layering of components is dominated by density.

Soft Spin Centrifugation

When whole blood is centrifuged at a low speed (up to 1,000 g) for a short time (two to four minutes), white cells sediment faster than red cells; and both sediment much faster than platelets (according to the Svedberg equation shown above). At higher speeds the same distribution is obtained in a shorter time. This produces layers of blood components that are not cleanly separated and consist of (1) plasma containing the majority of the suspended platelets and a minor amount of white cells and red cells, and (2) below that a thick layer of red cells mixed with the majority of the white cells and some platelets. The method of harvesting platelet-rich plasma (PRP) from whole blood is based on this principle. The term "platelet-rich" is used for this component because most of the platelets in the whole blood are in the plasma following slow centrifugation so the relative concentration of platelets in the plasma has increased.

Centrifugal sedimentation that takes the fractionation only as far as separation into packed erythrocytes and PRP is called a "soft spin." "Soft spin" is used herein to describe centrifugation conditions under which erythrocytes are sedimented but platelets remain in suspension. "Hard spin" is used herein to describe centrifugation conditions under which platelets sediment in a layer immediately above the layer of erythrocytes.

Two Spin Platelet Separation

Following a soft spin, the PRP can removed to a separate container from the erythrocyte layer, and in a second centrifugation step, the PRP may be fractioned into platelet-poor plasma (PPP) and platelet concentrate (PC). In the second spin the platelets are usually centrifuged to a pellet to be re-suspended later in a small amount of plasma or other additive solution In the most common method for PRP preparation, the centrifugation of whole blood for 2 to 4 min at 1,000 g to 2,500 g results in PRP containing the majority of the platelets. After the centrifugation of a unit (450 ml) of whole blood in a 3-bag system the PRP is transferred to an empty satellite bag and next given a hard spin to sediment the platelets and yield substantially cell-free plasma. This is termed "two-spin" platelet separation.

To recover the platelets following two-spin separation, most of the platelet poor plasma (PPP) is removed except for about 50 ml and the pellet of platelets is loosened and mixed with this supernatant. Optionally one can remove about all plasma and reconstitute with additive solution. To allow aggregated platelets to recover the mixture is given a rest of one to two hours before platelets are again resuspended and then stored on an agitator.

It is believed that two-spin centrifugation can damage the platelets by sedimenting the platelets against a solid, non-physiological surface. The packing onto such a surface induces partial activation and may cause physiological damage, producing "distressed" platelets which partially disintegrate upon resuspension.

Hard Spin Centrifugation

If the centrifugation is continued at a low speed the white cells will sediment on top of the red cells whereas the platelets will remain suspended in the plasma. Only after extended low speed centrifugation will the platelets also sediment on top of the red cells.

Experiments with a blood processor have shown that centrifugation at a high speed (2,000 g-3,000 g) produces a similar pattern of cell separation in a shorter time. Initially the cells separate according to size, i.e., white cells sediment faster than red cells and platelets remain in the plasma. Soon the red cells get 'packed' on each other squeezing out plasma and white cells. Because of their lower density, white cells and platelets are pushed upwards to the interface of red cells and plasma whereas the platelets in the upper plasma layer will sediment on top of this interface, provided the centrifugal force is sufficiently high and sedimentation time is sufficiently long. Plasma, platelets, white cells and red cells will finally be layered according to their density. Platelets sedimented atop a layer of red cells are less activated than those isolated by the "two spin" technique.

Leukoreduction

The PC's resulting from both two spin processing and apheresis methods contain donor leukocytes. In apheresis, centrifugal blood processing is a growing field, per-processing bowl and to pick up various centrifugally permitting the continuous removal of blood from a patient, separated components of the material during centrifugation then administration of the depleted blood back to the patient (U.S. Pat. No. 4,389,206, the entire contents of which are hereby incorporated herein by reference). The white cells negatively affect platelet storage and may induce adverse effects after transfusion due to cytokine formation. Removal of leukocytes (leukoreduction) from PRP and PC is important because non-self leukocytes (allogeneic leukocytes) and the cytokines they produce can cause a violent reaction by the recipient's leukocytes. In 1999 the FDA Blood Product Advisory Committee recommended routine leukoreduction of all non-leukocytes components in the US (Holme 2000). Therefore, much of the prior art focuses on leukoreduction of platelet concentrates because non-autologous leukocytes excite deleterious immune reactions. Since the process of this invention provides a convenient way to quickly harvest autologous platelets from the patient's blood, immune reactions are not a risk, and the presence of leukocytes is of little or no concern.

Plasma concentrates and their utility in hemostasis and wound healing have been described in U.S. Pat. No. 5,585,007. Plasma concentrates can be made in a two-step method, first separating of plasma from the majority of erythrocytes and then concentrating the plasma by removing water. The plasma can be separated from the erythrocytes by centrifugation. The water can be removed from the plasma using a semipermeable membrane or by contact with a desiccated hydrogel bead. The membrane and hydrogel bead pores allow passage of water, salts and other low molecular weight components while blocking passage of cells, platelets (thrombocytes), cell fragments and larger molecules such as fibrinogen. The passage of water and low molecular weight components through the membrane or into the bead concentrates the plasma, the cells and high molecular weight components contained therein. The dry hydrogel beads can be dextranomer or polyacrylamide.

Recent publications report that platelet preparations enhance the healing rate of hard and soft tissue defects. Activated cytokine proteins, released from activated platelets, signal the migration, proliferation and activation of monocyte cells. Monocyte cells sense a gradient of cytokines and migrate towards the source.

Fibers of polymerized fibrin form pathways by which monocyte cells translocate into the wound. Translocation is enhanced by tension on these fibers imparted by the action of platelet microtubules during clot retraction. Therefore, in situ polymerization of platelet-containing fibrinogen solutions provides an enhanced setting for wound healing. Platelet-plasma concentrates provide enhanced signals and pathways for wound healing cell migration.

Platelets have a limited half-time in vivo, and platelet activity declines rapidly ex vivo. An optimal wound healing compound therefore would contain freshly isolated platelets. To minimize risk of disease transmission and maximize beneficial patient response to platelet activity the platelet/plasma concentrate would preferably be prepared from the patient's own blood, i.e. autologously. The amount of blood withdrawn from the patient should be as small as possible to minimize morbidity caused by blood loss.

The invention of U.S. Patent Application Publication No. 2004/0182795 by Randel Dorian and Richard Storrs provides methods and apparatus for rapidly separating patient plasma from whole blood, contacting said plasma with dry hydrogel beads, concentrating said plasma, and separating the resulting plasma concentrate from the beads for application to patient wounds.

Dorian's invention relates to a device for preparing plasma concentrate from plasma containing cells (plasma cell mixture) comprising a centrifugal separation chamber having a plasma-cell mixture inlet port and a centrifugal separation chamber outlet port. The concentrating chamber has an inlet port and a concentrate outlet, the inlet port communicating with the centrifugal separation chamber outlet port, the concentrating chamber containing hydrogel beads and at least one inert agitator. The device also includes a concentrate chamber having an inlet communicating with the concentrate outlet through a filter, the concentrate chamber having a plasma concentrate outlet port. A plunger can be positioned in the concentrating chamber. The concentrating chamber has an inner concentrating chamber wall, the plunger having an outer edge surface conforming to a surface of the inner concentrating chamber wall; and the hydrogel beads and agitator can be positioned in the concentrating chamber between the plunger and the filter. The outer edge surface of the piston can form a sealing engagement with the surface of the inner concentrating chamber wall.

In one embodiment, the centrifugal separation chamber has an erythrocyte-plasma interface level, and the centrifugal chamber outlet port is positioned above the erythrocyte-plasma interface level. The concentrating chamber can have an unconcentrated plasma-air interface level, the centrifugal separation chamber outlet port and the concentrating chamber inlet port form an open passageway for flow of plasma, and the concentrating chamber inlet port is positioned at a level above said plasma-air interface level. Alternatively, the centrifugal separation chamber can have a one-way valve permitting flow of plasma from the centrifugal separation chamber into the concentrating chamber. In these embodiments, the agitator can be a dense object such as a smooth ball which can be a stainless steel. The filter can be a porous frit.

The term "plasma concentrate" is defined to include both plasma concentrate with platelets and plasma concentrate without platelets.

A method of Dorian's invention for producing plasma concentrate from plasma containing erythrocytes and platelets can comprise the steps of (a) centrifugally separating a plasma-cell mixture to form an erythrocyte-rich layer and a plasma layer; (b) moving the plasma from the plasma layer into a concentrating chamber containing hydrogel beads and an agitator to form a hydrogel bead-plasma mixture; (c) causing the agitator to stir the hydrogel bead-plasma mixture, minimizing gel polarization and facilitating absorption of water by the beads from the plasma, until a hydrogel bead-plasma concentrate is formed; and (d) separating plasma concentrate from the hydrogel beads from the hydrogel bead-plasma concentrate by passing the plasma concentrate through a filter. The hydrogel beads can have the effective absorption capacity to remove at least 10 percent of the water from the plasma, at least 25 percent of the water from the plasma, or at least 50 percent of the water from the plasma. The plasma containing erythrocytes and platelets can be whole blood.

Dorian's invention can be a method for producing plasma concentrate with a plasma concentrating device comprising a centrifugal separation chamber having a plasma-cell mixture inlet port and an centrifugal separation chamber outlet port; a concentrating chamber having a inlet port and a concentrate outlet, the inlet port communicating with the centrifugal separation chamber outlet port, the concentrating chamber containing hydrogel beads and at least one inert agitator; and a concentrate chamber having an inlet communicating with the concentrating outlet through a filter, the concentrate chamber having a plasma concentrate outlet port. With this device, the method can comprise (a) centrifuging a plasma-cell mixture in the centrifugal separation chamber to form an erythrocyte-rich layer and a plasma layer; (b) moving the plasma from the plasma layer through the separation chamber outlet port through the inlet port of the concentrating chamber to form a hydrogel bead-plasma mixture; (c) causing the agitator to stir the hydrogel bead-plasma mixture, minimizing gel polarization and facilitating absorption of water by the beads from the plasma, until a hydrogel bead-plasma concentrate is formed; and (d) separating plasma concentrate from the hydrogel beads from the hydrogel bead-plasma concentrate by passing the plasma concentrate through the filter and the concentrating chamber outlet port.

In Dorian's method, a plunger can be positioned in the concentrating chamber, the hydrogel beads and agitator are positioned in the concentrating chamber between the plunger and the filter, and the concentrating chamber has an inner concentrating chamber wall, the plunger having an outer edge surface conforming to a surface of the inner concentrating chamber wall. With this variation of the device, the method can comprise (a) centrifuging a plasma cell mixture in the centrifugal separation chamber to form an erythrocyte-rich layer and a plasma layer; (b) moving plasma from the plasma layer through the inlet/outlet port and the filter by axial movement of the plunger in the proximal direction away from the filter; (c) moving the plasma concentrating device in alternative distal and proximal directions along the central axis of the concentrating chamber to stir the hydrogel bead-plasma mixture, minimizing gel polarization and facilitating absorption of water by the beads from the plasma, until a hydrogel bead-plasma concentrate is formed; and (d) separating plasma concentrate from hydrogel beads by moving the plasma concentrate through the filter. In step (d) the plasma concentrate can be moved through the filter and into the concentrate outlet by moving the plunger in the distal direction toward the filter. Other means of moving the plasma concentrate through the filter are within the intended scope of this invention, such as movement by centrifugal force or suction, for example.

In U.S. Pat. No. 7,553,413, dated Jun. 30, 2009 entitled "PLASMA CONCENTRATOR DEVICE," the inventors Randel Dorian, Michael D. Leach and Richard Wood Storrs, the entire contents of which are hereby incorporated herein by reference, disclose a plasma concentrator of this invention having a concentrator chamber, concentrator gel beads, a filter, and an agitator. The agitator has agitator blades extending outwardly from the lower end. The agitator end is positioned in the concentrator chamber and supported for rotation about its central axis and for reciprocal movement along its central axis. The concentrator has a top with an upper opening through which the upper end of the actuator stem extends, and a lower opening in which the filter is positioned. The concentrator chamber can have a cylindrical inner wall, and the agitator blades can have an outer edge in close proximity to the inner wall with the space between the outer edge and the inner wall being less than the diameter of the gel beads. The filter is selected to block effective flow of plasma therethrough under ambient gravity conditions and permit plasma and plasma concentrate flow therethrough under centrifugal forces of the separation gravity. The method concentrates plasma by removing water without significantly denaturing the fibrinogen in the plasma. The plasma is introduced into a concentration chamber containing a plurality of dehydrated concentrator gel beads and an agitator. Then water is removed from the plasma while stirring the beads to reduce plasma polarization and breaking up clumps of beads that form during the agitation. Then centrifugal force can be applied to the concentrated plasma in an amount sufficient to separate a substantial portion of the plasma concentrate from the beads.

A major improvement in making plasma concentrate from whole blood for use in wound healing and as a tissue sealant is described in U.S. Pat. No. 5,585,007; this patent is hereby incorporated herein by reference in its entirety. This device, designed for placement in a medical laboratory or surgical amphitheater, used a disposable cartridge for preparing tissue sealant. The device was particularly applicable for stat preparations of autologous tissue sealants. Preparation in the operating room of 5 ml of sealant from 50 ml of patient blood required less than 15 minutes and only one simple operator step. There was no risk of tracking error because processing can be done in the operating room. Chemicals added could be limited to anticoagulant (e.g., citrate) and calcium chloride. The disposable cartridge could fit in the palm of the hand and was hermetically sealed to eliminate possible exposure to patient blood and ensure sterility. Adhesive and tensile strengths of the product were comparable or superior to pooled blood fibrin sealants made with precipitation methods. Use of antifibrinolytic agents (such as aprotinin) was not necessary because the tissue sealant contained high concentrations of natural inhibitors of fibrinolysis from the patient's blood. This new tissue sealant also optionally contained patient platelets and additional factors that promote wound healing, healing factors that are not present in commercially available fibrin sealants.

This device used a new sterile disposable cartridge with the separation chambers for each run. Since the device was designed to be used in a normal medical setting with ample power, the permanent components, designed for long-term durability, safety and reliability, were relatively heavy, using conventional centrifuge motors and accessories.

Small, self-contained centrifugal devices for obtaining platelet concentrates from blood are described in application Ser. No. 10/394,828 filed Mar. 21, 2003, the entire contents of which are hereby incorporated herein by reference. This device separates blood into erythrocyte, plasma and platelet layers and selectively removes the platelet layer as a platelet concentrate, that is, platelets suspended in plasma. The plasma fraction, being in an unconcentrated form, is not effective as a hemostat or tissue.

In a patent application entitled "Buoy Suspension Fractionation System" with the application Ser. No. 12/101,586 (Publication No. 2009/0014391 A1), filed on Apr. 11, 2008, the entire contents of which are hereby incorporated herein by reference, Leach discloses a separator that uses centrifugation to fractionate a suspension such as blood comprises a separation container and a buoy. The buoy is carried in the separation container and has a tuned density that is configured to reach an equilibrium position in a suspension. The guide surface is carried on the buoy upper surface and is inclined to an accumulation position near a buoy perimeter. The buoy suspension fractionation system can be used in a method of isolating a fraction from a suspension, and in a method for re-suspending particulates for withdrawal.

In patent application entitled "Apparatus and method for separating and isolating components of a biological fluid" having application Ser. No. 12/315,722 (Publication No. 2010/0140182 A1) and a filing date of Dec. 4, 2008, the entire contents of which are hereby incorporated herein by reference, Chapman et al. discloses that it is known to separate biological fluids, such as aspirated bone marrow or peripheral blood, into their component parts, fractions, phases, or constituent layers by centrifugation. It is also known to provide mechanical devices comprised of a tube which houses a solid separator which, when actuated by centrifugal force, allows biological fluid to flow through or around the piston based on differing relative densities thereby separating the biological fluid into a one or more component parts above and one or more component parts below the solid separator. For example, when the biological fluid within the tube is blood, the centrifugation process results in a high density layer of red blood cells below the solid separator, a low density layer of plasma above the solid separator, and a buffy coat layer which defines an intermediate density layer or third fraction above the solid separator and below the low density layer of plasma.

One of the earliest solid separators was disclosed in U.S. Pat. No. 3,508,653, issued Apr. 28, 1970 to Coleman, the entire contents of which are hereby incorporated herein by reference. That device was a rubber or other elastomeric cylinder. A major problem with that device was the inability to maintain a seal because it is costly to maintain the precise inner diameter of the test tube when mass produced. A subsequent solid separator development is disclosed in U.S. Pat. No. 3,814,248, issued Jun. 4, 1974 to Lawhead, the entire contents of which are hereby incorporated herein by reference. Next, U.S. Pat. No. 3,779,383, issued Dec. 18, 1973 to Ayres, the entire contents of which are hereby incorporated herein by reference, disclosed a device in which the blood introduction end of the tube is opposite to the movable separator end of the tube, and abutting an impenetrable rubber closure. Following Ayres, U.S. Pat. No. 3,931,018, issued Jan. 6, 1976 to North, Jr., the entire contents of which are hereby incorporated herein by reference, disclosed a solid separator for use in separation of blood serum and blood plasma using centrifugal force that must be inserted into the blood collection tube after blood collection.

In a patent to Levine, et al. (U.S. Pat. No. 4,159,896, issued Jul. 3, 1979), the entire contents of which are hereby incorporated herein by reference, a centrifugally motivated solid separator device is disclosed in which a cylindrical float is disposed inside of a tube, which float has an accurately controlled outside diameter so as to fit snugly in the tube bore under static conditions. When used in harvesting blood cells the float is formed with an axial through bore which receives and expands the white cell and platelet layers in the blood sample after centrifugation thereof. The disclosed float was made from a plastic material having a specific gravity that causes it to float in the packed red cells after centrifugation of the blood sample in the tube.

In another patent to Levine, et al, (U.S. Pat. No. 5,393,674, issued Feb. 28, 1995), the entire contents of which are hereby incorporated herein by reference, a clear plastic tube large enough to process 1 ml of blood and equipped with a cylindrical float and filled with an inert gas at low pressure is disclosed. The float contains a through bore, and prior to centrifugation, is held fixably at an initial location by tight contact between the exterior of the float and the interior wall of the tube. Unlike the inventions of Coleman, which contain pistons (or buoys) with no through bore, the Levine float relocates, under centrifugation, to a new position determined by its density relative to the density of the blood fractions as a result of the shrinkage of its diameter due to the longitudinal elongation (and subsequent lateral narrowing) of the float body that results from the substantial gravity gradient that occurs from the top to the bottom of the float. This substantial G force gradient (several thousand Gs) causes the float to elongate and narrow just as a rubber tube elongates and narrows when pulled from both ends. This space between the exterior of the float and the interior of the tube that develops during centrifugation provides the freedom of movement of the float consequent with the motion of the blood components to their new location determined by their density relative to the float. Levine does not posit, but it is assumed that some of the redistributing blood components also travel through the bore during centrifugation but since the top and bottom of the through bore are not closed, any cells and platelets that wind up there following centrifugation are easily infiltrated by the red cells and plasma during normal post centrifugation handling. Designed predominately as a diagnostic tool that proceeds through the visual examination of the cells that at least temporarily occupy the through bore right after centrifugation, Levine also discloses the possibility of extracting these cells with a syringe needle for additional diagnostic examination. This method of extraction necessarily is inefficient as a means of cell recovery as the intruding needle necessarily relocates the target cells above and below the through bore as it is inserted.

Hence, these known mechanical devices are generally capable of separating biological fluids into component parts or fractions; however, these devices are not very precise thereby resulting in inefficient separation of the biological fluid into component parts or fractions because of the substantial commingling of the separated fractions. Additionally, these known mechanical devices fail to provide a simple or efficient method to extract a fraction other than the top fraction of the sample leading to low recoveries, especially of the clinically important buffy coat fraction.

It is also known to provide more complicated mechanical devices in an attempt to alleviate the above known problems. For example, the patent to Leach, et al. (U.S. Pat. No. 7,374,678, issued May 20, 2008), the entire contents of which are hereby incorporated herein by reference, in a first embodiment, discloses a device for separating a sample, such as blood, into a plurality of fractions. The device is comprised of a plunger (or second piston) which, prior to centrifugation, is retained proximate a top end of a closed ended distortable tube during centrifugation and a first piston (or buoy) which is tightly fitted near the bottom of the closed ended distortable tube such that under centrifugation with a sample of blood, the tube wall longitudinally compresses and bows outward thereby allowing the buoy to move in a direction of the top of the tube lifted by a layer of red blood cells of higher density than the piston that has flowed downward between the buoy and the interior of the tube wall. After centrifugation, the tube wall returns to its original dimension and traps this first piston at a new location coinciding with the interface position of a top plasma fraction and a bottom red blood fraction of the separated sample. On or near a collection face of this first piston (or buoy) is a third fraction which includes "a small, yet concentrated, amount of red blood cells, white blood cells, platelets, and a substantial portion of a buffy coat of the blood sample." The device then employs a plunger (or second piston) which is manually pushed down into the tube from a location proximate the top end of the tube. The plunger (or second piston) includes a valve which allows the plasma to pass through the plunger to while the plunger is lowered to a predetermined depth above the first piston set by a depth gauge which locates the plunger a distance away from the collection face of the piston thereby defining a third fraction between a bottom face of the plunger (or second piston) and the collection face of the first piston. The extraction of the third fraction is accomplished via a vacuum created on a tube extending between a collection valve disposed in the top of the tube and a bore extending from the top of the plunger and the bottom of the plunger.

Accordingly, this device relies on the imprecise longitudinal compression and decompression of the tube wall in order to control the flow path between fractions and fails to contain the separated fractions until after centrifugation stops and the tube wall returns to its original dimensions. Furthermore, the extraction of the third fraction requires infiltration of the top plasma fraction. Hence, this recently patented device still fails to alleviate the problem of inefficient separation of the biological fluid into component parts or fractions and the commingling of the separated fractions.

In another embodiment, Leach, et al. discloses that the plunger (or second piston) is rigidly or slideably fitted with the first piston or buoy such that the pair is tightly fitted within the closed ended distortable tube wherein under centrifugation with a sample such of blood, the tube wall bows outward thereby allowing the pair to move in a direction of the top of the tube while lifted by a high density layer of red blood cells flowing downward between the pair and the interior of the tube wall. After centrifugation, the tube wall returns to its original dimension which grips the periphery of the first piston at an interface position of a plasma fraction and a red blood fraction of the separated sample. On or near a collection face of this first piston is "a small, yet concentrated, amount of red blood cells, white blood cells, platelets, and a substantial portion of a buffy coat of the blood sample." The extraction of the intermediate (buffy coat) or third fraction is accomplished "by interconnecting a cannula or bored tube with the connection portion of the buoy cylinder" and connecting an extraction syringe to the cannula for creating a vacuum to draw the intermediate or third fraction from the space between the first and second pistons. This embodiment describes only one centrifugation spin, and fails to alleviate the problem of inefficient separation of the biological fluid into component parts or fractions and the commingling of the separated fractions. Furthermore, the extraction of a fraction other than the top fraction still requires the infiltration of at least one other fraction than the desired fraction to be extracted. Moreover, the device relies on the imprecise longitudinal compression and decompression of the tube wall in order to control the flow path between fractions and fails to contain the separated fractions until centrifugation stops and decompression of the tube wall is concluded.

Another problem associated with both embodiments of Leach, et al. is that the collection face, trough, or sump of the buoy must be shallow to be at a desired density level of the target buffy coat fraction and to preclude even further accumulation of reds cells with the target white cells and platelets to be extracted. Thus, this shallow trough results in having the target white blood cells and platelets, come to rest on the entire large surface area of the first piston on which the white blood cells and platelets tend to stick, which reduces the efficiency of the final collection step. A further problem associated with both embodiments of Leach, et al. is the time consuming and laborious process of fitting and interconnecting multiple parts to the device in order to perform the extraction process.

In general, current processes for separating and extracting fractions out of biological fluids require multiple steps that are both laborious and time consuming and that result in poor recoveries of the target white cells and platelets. Hence, it would be desirable to provide a simplified and more effective process so less time, labor, and training is required to do the procedure and fewer white cells and platelets are lost thereby providing a positive economic impact. A simplified process would also allow it to be performed in an intra-operative setting by an operating room nurse, rather than a remote laboratory setting by a technician so that a patient can be more rapidly treated and the possibility of mixing up samples can be essentially eliminated. Process simplification also has a direct correlation to process reproducibility that is also a problem with the known prior art.

Hence, the known prior art is problematic in a number of areas which include a deficiency in the recovery efficiency of cells of interest (target cells), in the selectivity of separation for reducing contamination or non-target cells from the target cell population, and in the multiple step, laborious, and time consuming extraction process. A summary of the invention of Chapman disclosed in application Ser. No. 12/315,722 is a device for separating and isolating components of a biological fluid comprising a container for containing the fluid to be processed, a tube cap assembly for closing the container while providing filling and extraction communication therewith, a float assembly disposed within the container for funneling and controlling biological fluid flow into an inverted domed shaped isolation chamber within the float and controlling the biological fluid flow out of the isolation chamber for effecting an encapsulation or a sealed isolation of at least one component or fraction of the biological fluid flow within the isolation chamber during a centrifugation process. The device further comprising a flexible tube for connecting an extraction passageway disposed within the float assembly and an extraction valve of the tube cap assembly for allowing extraction of at least the one component or fraction encapsulated or isolated within the chamber.

The Goddard et. al in U.S. Patent Application Publication No. 2007/0259330 A1 published on Nov. 8, 2007, the entire contents are incorporated herein by reference, describe an invention that relates to the field of cell separation, and more specifically to a method of separating mononuclear cells from blood. The Goddard invention also encompasses a separation media which is used in the present method, a container filled with such media and a kit useful in cell separation.

U.S. Pat. No. 5,474,687 (Activated Cell Therapy), the entire contents are incorporated herein by reference, relates to the enrichment of CD34+ cells. More specifically, a method is disclosed, which comprises layering a cell mixture containing CD34+ cells into a centrifuge tube, said density gradient solution having an osmolality of 280±10 mOsm/kg H2O and a specific density within 0.0005 g/ml of the specific density of said CD34+ cells; centrifuging said tube at a gravitational force sufficient to pellet cells having specific densities greater than the specific density of the density gradient material in said tube; and collecting from the upper portion of said tube an enriched population of CD34+ cells. The tube used in the method comprises an annular member disposed in said tube and defining an opening there through, which opening has an area less than the area of a cross section of the tube.

In one embodiment, the method further comprises incubating said cell mixture with a cell type-specific binding agent linked to carrier particles prior to centrifugation, said particles having a specific density that is at least 0.001 g/ml greater than the specific density of said density gradient solution. This binding agent may bind to non-CD34+ cells, and may e.g. be an antibody directed to the CD45 antigen. The density gradient solution may e.g. be selected from the group consisting of Percoll™, Ficoll™, Ficoll-Hypaque™, albumin, sucrose and dextran. As appears from the above, there is still a need in this field of novel purification protocols which allow efficient purification of viable mononuclear cells from blood in yields useful for clinical applications.

The invention of Vlasselaer disclosed in U.S. Pat. No. 5,474,687 dated Dec. 12, 1995, the entire contents are incorporated herein by reference, relates to methods of enriching hematopoietic progenitor cells from body fluids. In particular, it relates to the use of a cell-trap centrifugation tube containing a gradient solution adjusted to a specific density to enrich for CD34+ cells from aphresed blood. The tube allows the desired cell population to be collected by decantation after centrifugation to minimize cell loss and maximize efficiency. In addition, the method can be further simplified by density-adjusted cell sorting which uses cell type-specific binding agents such as antibodies and lectins is linked to carrier particles to impart a different density to undesired cell populations allowing the progenitor cells to be separated during centrifugation in a more convenient manner. The rapid progenitor cell enrichment method described herein has a wide range of applications, including but not limited to, donor cell preparation for bone marrow transplantation without the use of invasive procedures such as bone marrow aspiration.

The invention of Inbar et al. disclosed in U.S. Pat. No. 5,314,074 dated May 24, 1994 entitled "Method and Means for Density Gradient Centrifugation," the entire contents are incorporated herein by reference, discloses a method and means for density gradient centrifugation.

U.S. Pat. No. 4,824,560, the entire contents are incorporated herein by reference, discloses method and means for centrifugation by which a tubular vessel is used with at least two compartments in a row communicating with one another via a narrow, essentially capillary opening. For operation, the working fluid is charged into the lower compartment and the liquid to be centrifuged into the upper one with no need for any special precautions to avoid mixing prior to centrifugation. While this method has some significant advantage over the above-described purely manual methods, it has the drawback that the rather narrow passage between the compartments provides some resistance even during centrifugation which may prolong the operation. Moreover, the method requires specially devised centrifugation vessels which renders it relatively costly. Furthermore, since in accordance with that method the entire lowermost compartment must be filled with working fluid it is not possible to vary the amount of working fluid in a given centrifugation vessel.

In 2008, C. Nilsson, et al. published a paper entitled "Optimal Blood Mononuclear Cell Isolation Procedures for Gamma Interferon Enzyme-Linked Immunospot Testing of Healthy Swedish and Tanzanian Subjects" in Clin Vaccine Immunol. 15(4): 585-589, the entire contents are incorporated herein by reference, in which they compared different existing methods of density gradient separation of peripheral blood.

It is known in the prior art to digest tissues to release cells. Such cell suspensions can be made from surgically removed tumors or from normal tissue such as adipose. Gimble et al published a review manuscript in Circulation Research 100 (9) 1249-60 entitled "Adipose-derived stem cells for regenerative medicine" for which the entire contents are incorporated herein by reference, which reviews the known art of cell isolation and mechanical devices for adipose tissue processing. References cited refer to article references found in the publication of Gimble.

The initial methods to isolate cells from adipose tissue were pioneered by Rodbell and Rodbell and Jones in the 1960s. They minced rat fat pads, washed extensively to remove contaminating hematopoietic cells, incubated the tissue fragments with collagenase, and centrifuged the digest, thereby separating the floating population of mature adipocytes from the pelleted stromal vascular fraction (SVF). The SVF consisted of a heterogeneous cell population, including circulating blood cells, fibroblasts, pericytes, and endothelial cells as well as "preadipocytes" or adipocyte progenitors. The final isolation step selected for the plastic adherent population within the SVF cells, which enriched for the "preadipocytes."

Subsequently, this procedure has been modified for the isolation of cells from human adipose tissue specimens. Initially, fragments of human tissue were minced by hand; however, with the development of liposuction surgery, this procedure has been simplified. During tumescent liposuction, plastic surgeons infuse the subcutaneous tissues with a saline solution containing anesthetic and/or epinephrine via a cannula and then remove both the liquid and tissue under suction. The procedure generates finely minced tissue fragments, the size of which depends on the dimensions of the cannula. Independent studies have determined that liposuction aspiration alone does not significantly alter the viability of isolated SVF cells. Indeed, adherent stromal cells with characteristics of adipocyte progenitors can be found directly within the liposuction aspiration fluid, as well as in SVF derived from the tissue fragment digests. However, when ultrasound-assisted liposuction is performed, the number of cells recovered from tissue digests is reduced, as is their proliferative capacity. The recovery of ASCs can be improved further by manipulating the centrifugation speed. Investigators have achieved optimal cell recovery using a centrifugation speed of 1200 g based on the subsequent formation of a human-derived adipose tissue depot following implantation in an immunodeficient murine model.

The cell isolation process requires the manipulation of large volumes of lipid-laden cells, presenting potential risks to equipment and personnel. To facilitate the process, several groups have fabricated devices to automate the cell isolation. One approach uses a "bag within a bag." The suctioned aspirate flows through a central bag that automatically sieves the tissue while draining away the aspiration fluid. Subsequently, the trapped tissue can be washed and further manipulated. Others have developed a closed, rotating, controlled temperature incubator capable of collagenase digesting and separating up to one liter of tissue at a time. These prototypes may one day lead to commercially available manufactured devices for large scale, automated adipose tissue manipulation and cell isolation suitable for clinical applications.

Collas discloses a protocol for separation of the stromal vascular fraction from adipose consists of the following steps:

Lipoaspirate Washing

It is necessary to wash the lipoaspirate extensively to remove the majority of the erythrocytes and leukocytes. The following procedures should be performed under aseptic conditions. Place a maximum of 300 ml of lipoaspirate into a used sterile medium bottle. Allow the adipose tissue to settle above the blood fraction. Remove the blood using a sterile 25 ml pipette. Add an equivalent volume of HBSS with antibiotics and fungizone and firmly tighten the lid. Shake vigorously for 5-10 seconds. Place the bottle on the bench and allow the adipose tissue to float above the HBSS. This will take 1-5 min depending on the sample.

Carefully remove the HBSS using a 50 ml pipette. Repeat the above washing procedure (steps 4 to 7) three times. Medium from the final wash should be clear. If it is still red, wash again by repeating steps 4.

Collagenase Digestion

Dispersion of adipose tissue is achieved by collagenase digestion. Collagenase has the advantage over other tissue digestive enzymes that it can efficiently disperse adipose tissue while maintaining high cell viability. Make up collagenase solution just prior to digestion. The final volume required is half that of the washed adipose tissue volume. Add powdered collagenase to HBSS at a final concentration of 0.2%. We dissolve the required amount of collagenase into 40 ml of HBSS, then filter sterilize into the remaining working volume. Add antibiotics and fungizone. Add the washed adipose tissue to large cell culture flasks (100 ml per 162 cm2 flask). Add collagenase solution. Re-suspend the adipose tissue by shaking the flasks vigorously for 5-10 seconds. Incubate at 37° C. on a shaker for 1 to 2 h, manually shaking the flasks vigorously for 5-10 seconds every 15 min. During the digestion, prepare Histopaque gradients by dispensing 15 ml of Histopaque-1077 into 50 ml tubes. Two gradients are required for each 100 ml of washed adipose tissue. The gradients must be equilibrated at room temperature before use. Prepare 200 ml of washing medium consisting of HBSS containing 2% FBS, antibiotics and fungizone. On completion of the digestion period, the digested adipose tissue should have a "soup like" consistency. Add FBS to a final concentration of 10% to stop collagenase activity.

Separation of the Stromal-Vascular Fraction

After digestion, the ability of lipid-filled adipocytes to float is used to separate them from the stromal vascular fraction (SVF). Dispense the collagenase-digested tissue into 50 ml tubes. Avoid dispensing undigested tissue. Centrifuge at room temperature at 400×g for 10 min. After centrifugation, use a 50 ml pipette to aspirate the floating adipocytes, lipids and the digestion medium. Leave the SVF pellet in the tube.

Separation of Stromal Stem Cells from the SVF

The SVF predominantly contains erythrocytes, leukocytes, endothelial cells and stromal stem cells. Erythrocytes are removed first, using the red blood cell lysis buffer.

Removal of erythrocytes. Re-suspend thoroughly each SVF pellet in 20 ml of cell lysis buffer at room temperature. Incubate at room temperature for 10 min. Centrifuge at 300×g for 10 min and aspirate the cell lysis buffer.

Removal of cell clumps and remaining undigested tissue. It is essential to obtain a cell suspension free from undigested tissue and cell clumps, to effectively separate stromal stem cells from other cell types using antibody-conjugated magnetic beads. The strategies used to achieve this are separation of gross undigested tissue using gravity, straining of cells and gradient separation. Re-suspend SVF pellets thoroughly in 2 ml of washing medium using a 1 ml pipette. Pipet the cells up and down several times to reduce clumping. Pool the pellets into two 50 ml tubes. Allow undigested tissue clumps to settle by gravity for ~1 min. Aspirate and pass the suspended cells through 100 μm cell strainers. Pass the filtered cells through 40 μm cell strainers. Add extra washing buffer so that the final volume is equivalent to that of the gradients (i.e., for 4 gradients, the volume of cells in washing buffer should be 60 ml).

Ficoll Separation

Hold each tube containing Histopaque at a 45 degree angle and carefully add the cells by running the suspension along the inside wall of the tube at a flow rate of ~1 ml per second. Careful layering of cells onto the gradients is essential for successful cell separation. Centrifuge gradients at exactly 400×g for 30 min. Carefully remove the medium (~10 ml)

above the white band of cells found at the gradient interface and discard. Carefully remove the white band of cells (~5 ml) by careful aspiration and place into a new 50 ml tube. Add an equivalent volume of washing medium and centrifuge at 300×g for 10 min using a low brake setting. Aspirate and re-suspend each pellet in 25 ml of washing medium. Centrifuge at 300×g for 10 min using a low brake setting.

Separation of stromal stem cells from endothelial cells and leukocytes by magnetic cell sorting.

Stromal stem cells are separated from remaining cells using magnetic cell sorting. Unwanted endothelial (CD31+) and leukocytes (CD45+) are magnetically labeled and eliminated from the cell suspension when applied to a column under a magnetic field. Magnetically labeled cells are retained in the column, while unlabeled stem cells with a CD45-CD31- phenotype pass through the column and are collected. To this end, CD31+ and CD45+ cells are labeled with FITC-conjugated anti-CD31 and anti-CD45 antibodies. The stained cells are magnetically labeled by the addition of anti-FITC-conjugated magnetic micro-beads. This approach presents the advantage that cell purity after separation can be assessed by flow cytometry or fluorescence microscopy. For the following steps, use cold buffer and work on ice to reduce cell clumping. Re-suspend and pool the sedimented pellets in 10 ml of column buffer (PBS containing 2 mM EDTA and 0.5% BSA). Remove all remaining cell clumps by passing the suspension through a 40 μm cell strainer. Perform a cell count. Transfer cells to a 15 ml tube and centrifuge at 300×g for 10 min at 4° C. using a low brake setting. Re-suspend the cell pellet in column buffer and label with anti-CD31 FITC-conjugated and anti-CD45 FITC-conjugated antibodies according to the manufacturer's recommendations. Suspend cells in 100 μl of column buffer and add 10 μl of each antibody per 10$^7$ cells. Mix well and incubate for 15 min in the dark at 4° C. (re-suspend the cells after 7 min of incubation). Wash the cells to remove unbound antibody by adding 2 ml of column buffer per 10$^7$ cells. Centrifuge at 300×g for 10 min at 4° C. using a low brake setting. Aspirate the supernatant completely and re-suspend the cell pellet in 90 μl of column buffer per 10$^7$ cells. Add 10 μl of MACS anti-FITC magnetic micro-beads per 10$^7$ cells. Mix well and incubate for 15 min at 4° C. (re-suspend the cells after 7 min of incubation). Wash the cells to remove unbound beads by adding 2 ml of column buffer per 10$^7$ cells. Centrifuge at 300×g for 10 min at 4° C. using a low brake setting. Aspirate the supernatant completely and re-suspend the cell pellet in 500 μl of column buffer. For magnetic cell separation, we use the MACS LD column specifically designed for the depletion of unwanted cells. Place a MACS LD column onto the MidiMACS separation unit or onto a compatible unit. Prepare the column by washing with 2 ml of column buffer. Apply the cell suspension to the column and collect the flow-through unlabeled cells in a 15 ml tube. Wash unlabeled cells through the column by twice adding 1 ml of column buffer. Collect the total effluent. Check for stem cell purity If higher purity is required, centrifuge the collected cells at 300×g for 10 min at 4° C. using a low brake setting and repeat steps 11-17. Perform a cell count. Centrifuge at 300×g for 10 min at 4° C. using a low brake setting. Use the cells as required or freeze the cells according to standard protocols.

A patent was awarded to Fraser et al. in U.S. Pat. No. 7,390,484 on Jun. 24, 2008 entitled "Self Contained Adipose Derived Stem Cell Processing Unit" for which the entire contents are incorporated herein by reference.

A paper was published by Conde-Green et al. entitled "Effects of Centrifugation on Cell Composition and Viability of Aspirated Adipose Tissue Processed for Transplantation" in the Aesthetic Surgery Journal vol. 30 no. 2 249-255, 2010 for which the entire contents are incorporated herein by reference. The authors state centrifugation is one of the preferred methods of fat processing. Although it has been promoted for nearly three decades to separate adipose tissue components before grafting, there remain many controversies regarding the results obtained with centrifuged adipose tissue. In this paper, the authors demonstrate the effects of centrifugation on the cellular components of aspirated fat.

To do the study, fat harvested from the lower abdomen of 10 female patients undergoing liposuction was divided in two equal parts, then processed by decantation or centrifugation and sent to the laboratory. Each processed lipoaspirate was analyzed histologically after hematoxylin and periodic acid-Schiff staining for the presence of intact adipocytes. It was then cultured and analyzed by multicolor flow cytometry for identification of adipose-derived mesenchymal stem cells.

The authors found the middle layer of the centrifuged lipoaspirate, which is used by many surgeons, showed a great majority of altered adipocytes and very few mesenchymal stem cells in comparison with the decanted sample, which maintained the integrity of the adipocytes and showed a greater number of mesenchymal stem cells. The pellet observed as a fourth layer at the bottom of the centrifuged lipoaspirate showed the greatest concentration of endothelial cells and mesenchymal stem cells, which play a crucial role in the angiogenic and adipogenic effect of the grafted tissue. It was concluded that if centrifuged lipoaspirate is used, the pellet (rich in adipose-derived mesenchymal stem cells) and the middle layer should be employed to increase fat graft survival.

Xie et al. published a paper entitled "The effect of centrifugation on viability of fat grafts: an evaluation with the glucose transport test" in Journal of Plastic, Reconstructive & Aesthetic Surgery 63(3) 482-487, 2010 for which the entire contents are incorporated herein by reference.

The authors state that an up-to-date, simple, but useful technique to evaluate the viability of fat grafts prior to transplant is lacking. The purpose of this study is to introduce the glucose transport test—a new method to evaluate the viability of fat grafts after they are subjected to different centrifugal forces in vitro.

To conduct the their study, fat grafts were harvested from healthy patients who underwent liposuction for body contouring. The glucose transport test was performed to evaluate the viability of fat grafts after centrifugation with different forces (1000-4000 rpm). An MTT assay was also performed with the same experimental protocol for comparison. Routine histological examination was done in all groups to examine possible structural destruction after centrifugation.

When compared with the group not subjected to centrifugation, the glucose transport test showed a significant decrease in viability of fat grafts in all of the other four groups (all $p<0.001$). There was a linear reduction of viability in fat grafts with the increase in centrifugal force (all $p<0.03$). MTT assay showed similar findings on the viability of fat grafts in all five groups and correlated well with the glucose transport test ($r=0.9870$). Histology showed significantly distorted and fractured adipocytes when the centrifugal force reached 4000 rpm. The authors conclude their study demonstrates the harmful effect on the viability of fat grafts with an increase in centrifugal force and, for the first time, that the glucose transport test may be an effective and potentially useful method to evaluate the viability of fat grafts in a clinical setting.

Anderson et al. was awarded U.S. Pat. No. 6,346,421 on Feb. 12, 2002 entitled "Methods for Concentrating and Detecting Microorganisms Using Centrifuge Tubes," for which the entire contents are incorporated herein by reference.

Graham et al were awarded U.S. Pat. No. 4,436,631 on Mar. 13, 1984 entitled "Multiple Particle Washing System and Method of Use" for which the entire contents are incorporated herein by reference. Graham discloses a particle washing system and method of use is wherein in a preferred embodiment the fluid containing the desired particles is placed within an inner tube having near the bottom thereof an orifice with a diameter at least equal to that of the diameter of the particles, and wherein the inner tube is positioned within an outer tube having a fluid with a density at least equal to that of the solution containing the particles to be separated but less than that of the particles.

The application of centrifugal force to the particles directed toward the bottom of the outer tube causes the particles to move through the orifice and through the outer solution contained within the outer tube so that the particles are collected from the inner solution, washed by the outer solution, and subsequently sedimented at the bottom of the outer tube. Graham's invention has the stated objective to permit the rapid separation of particles from a solution in a "one step" operation. It is another objective that during separation of the particles from the solution containing the particles, the particles are washed so as to remove any nonspecific serum coating and to dilute any solute drag. It is yet another object that the original containing solution be separately maintained from the resulting particle concentration to permit the removal of the original mother solution in order to reduce contamination. It is another object to permit the separation of particles having different densities and dispensing at least one of such particle types to the exclusion of the sucrose typically having a molecular weight of 5,000 or more. The serum albumin may be selected from the group consisting of animal serum albumin and human serum albumin. Serum albumin, to be compatible, cannot have human gamma globulin or human complement.

The volumes of the washing solution and mother solution are chosen so that the interface between these solutions is contained within the inner hollow tube. Upon the application of centrifugal force, the particles contained within the mother solution, placed within the cavity formed by the hollow inner cylinder, are forced to move through the mother solution towards the bottom of the test tube in accordance with the sedimentation coefficients or Svedberg Units characterizing the particles. Since the hollow interior cylinder is merely resting upon the bottom of the outer test tube, the washing solution is capable of penetrating into and out of the inner hollow cylinder and is consequently, partially displaced.

It is still another objective of the present invention that these objectives be accomplished in a simple system capable of economical production and employable within simple, inexpensive centrifuges commonly available. It is still yet another objective that the apparatus and methodology of the present invention be capable of replacing expensive automated cell washers presently available. It is a further objective of the present invention to not only provide methodology whereby the objectives may be accomplished but also devices capable of meeting the desired objectives.

Rimm et al were awarded U.S. Pat. No. 6,197,523 on Mar. 6, 2001 entitled "Method for the Detection, Identification, Enumeration, and Confirmation of Circulating Cancer and/or Hematologic Progenitor Cells in Whole Blood" for which the entire contents are incorporated herein by reference. Rimm's method for analyzing blood enables one to isolate, detect, enumerate and confirm under magnification the presence or absence of target cancer cells and/or hematologic progenitor cells which are known to circulate in blood. The analysis is performed in a sample of centrifuged anti-coagulated whole blood. The analysis involves both morphometric and epitopic examination of the blood sample while the blood sample is disposed in a centrifuged blood sampling tube.

The epitopic analysis of the presence or absence of cancer cells relies on the detection of epitopes which are known to present only on cancer cells; and the epitopic analysis of the presence or absence of hematologic progenitor cells relies on the detection of epitopes which are known to present only on hematologic progenitor cells. The targeted epitopes on the target cell types are epitopes which are also known to be absent on normal circulating blood cells; and the target cancer cell epitopes are epitopes which are known to be absent on target hematologic progenitor cells. Fluorophors with distinct emissions are coupled with antibodies which are directed against the targeted epitopes.

The morphometric analysis is performed by staining the cells in the blood sample with an intracellular stain such as acridine orange which highlights the intracellular cell structure. Both the morphometric and epitopic analyses are preferably performed at or near the platelet layer of the expanded buffy coat in the centrifuged blood sample. The morphometric analysis and/or the epitopic analysis may be performed under magnification both visually and/or photometrically.

Rimm's invention relates to a method and assembly for the detection, identification, enumeration and confirmation of circulating cancer and/or hematologic progenitor cells in an anti-coagulated whole blood sample which is contained in a transparent sampling tube assembly. The detection, identification, enumeration and confirmation steps can all be performed in situ in the sampling tube assembly. More particularly, the method of this invention involves the centrifugal density-based separation of the contents of the blood sample in a manner which will ensure that any circulating cancer and/or hematologic progenitor cells in the blood sample are physically displaced by their density into a predetermined axial location in the blood sample and in the sampling tube assembly, and also into a restricted optical plane in the sampling tube assembly which is adjacent to the wall of the sampling tube, and finally into a very well defined zone of that optical plane.

Babson was awarded U.S. Pat. No. 4,639,242 on Jan. 27, 1987 entitled "Vessel and Procedure for Automated Assay" for which the entire contents are incorporated by reference. A number of procedures in the clinical laboratory require centrifugation. Examples include clarification of samples by removal of sediments or cells and removal of interfering proteins by specific precipitating reagents. In such cases the desired supernatant solution is normally decanted from the centrifuge tube to a clean tube for further processing. The present invention allows complete physical separation of the precipitate and supernatant solution in a single tube so that the supernatant solution can further be treated or sampled as by pipetting without disturbing the precipitate.

Hydrolytic enzymes can be measured by their action on insoluble substrates or soluble substrates that can be precipitated and separated from soluble products of hydrolysis. These assays can be performed in vessels of the present invention with fewer steps and/or reagents than is customarily used.

The reaction vessel shown in the patent may optionally be fabricated to contain a longitudinally extending divider within the interior of the bottom of the vessel. This divider will provide the interior of the vessel with a left reagent chamber and a right reagent chamber. When using this alternative form of Vessel 1, it is possible to place a first reactant in one reagent chamber and a second reactant in the second reagent chamber without causing interaction between the reagents. The reaction may then be started by tilting the vessel to allow the reagents in each chamber to mix, or by rapidly spinning the vessel about its longitudinal axis thereby causing the reactants to flow upward along the inside walls of the vessel and to mix during the spinning process.

The vessel 1 contains a collection chamber portion located near the uppermost portion of the vessel. This chamber is formed by an increase in their interior diameter of the vessel between two outwardly extending shoulders.

In a contemplated use by the inventors, the reaction vessel will act as a centrifuge tube spun about it longitudinal axis. If so spun, the contents will be forced towards the wall of the vessel be centrifugal force. As the vessel is tapered from a smaller lower diameter to a lower diameter to larger upper diameter the centrifugal force can be separated into two vectors: the major vector perpendicular to the vessel wall and a smaller vector in the upward direction parallel to the vessel wall. If the latter force exceeds one gravity the tube contents will be transferred entirely to the upper cylindrical portion of the vessel where the heavier solids contained in the fluid will be deposited on the vessel wall. If the upward force vector is less than one gravity the vessel contents will remain entirely in the lower portion, assuming the vessel has not been overfilled.

The amount of centrifugal force required to exceed one gravity in the vertical direction is related to the degree of taper in the mid-portion of the vessel, the greater the taper the greater the vertical force vector and the less total centrifugal force required. The centrifugation speed required to achieve that centrifugal force is inversely related to achieve that centrifugal force is inversely related to the diameter of the vessel according to the following formula: $rcf=5.585\ d(rpm/1000)^2$.

Pahuski et al. were awarded U.S. Pat. No. 5,700,645 on Dec. 23, 1997 entitled "Methods and kits for separation, concentration, and analysis of cells" for which the entire contents are incorporated by reference.

Nielsen et al. were awarded U.S. Pat. No. 4,511,349 on Apr. 16, 1985 entitled "Ultracentrifuge Tube with Multiple Chambers" for which the entire contents are incorporated by reference.

A patent was awarded to Glover et al. entitled "Vacutainer with Positive Separation Barrier" U.S. Pat. No. 3,879,295 in 1975, for which the entire contents are incorporated herein by reference. Glover teaches that an improved device for separating serum from cells preferably embody or provide a number of desirable attributes e.g., (1) obtaining a sample of blood and achieving separation of the two phases under sterile conditions; (2) minimizing the risk of loss of identity of the donor; (3) minimizing the migration of cells once the blood has been stratified into cells and serum; (4) utilizing, storing, or transporting the serum without interplay between the serum and the cells; (5) economic feasibility in manufacturing a disposable device; (6) the ability physically separate the container at a particular location determinable by the purpose of the test; (7) rapidity and simplicity in inserting the physical barrier to separate the serum from the cells.

SUMMARY OF THE INVENTION

With this invention a vessel is provided for use in a centrifuge which utilizes unique geometry to enable more rapid separation of the sample into fractions of different densities and to maintain such fraction separation after centrifugation. The vessel includes an interior space contained within an outer wall. A barrier divides this interior space of the vessel into at least two regions. These two regions are joined together over a top of a lip of the barrier defining an uppermost portion of the barrier, so that the two regions come together on an upper portion of the vessel but are spaced from each other on a lower portion of the vessel.

The vessel has a higher gee side and a lower gee side, respectively defined by the portion of the vessel most distant from a spin axis of the centrifuge and closest to the spin axis of the centrifuge, when the vessel is positioned within a cradle or other vessel support of the centrifuge. The barrier is oriented to divide the interior space of the vessel into the higher gee region and the lower gee region. Thus, after centrifugation is complete, and spinning of the centrifuge stops, higher density fractions remain on a higher gee side of the barrier with lower density fractions remain on the lower gee side of the barrier.

Furthermore, sample separation can be enhanced and accelerated by providing a face of the barrier closest to the spin axis with a taper. This taper is selected so that portions of the face closest to the lip are most distant from the spin axis with portions of the face most distant from the lip closest to the spin axis. This taper can be flat or curving, such as a concave curve, with different contours on the face adjusting the separation rate.

The vessel benefits from being configured for the specific sample to be separated. In particular, the lip of the barrier can be positioned and/or the region volumes selected to match expected percentage constituents of each fraction within the sample. This correlation can be exact or merely general in nature. With such vessel optimization, the barrier maintains separation of the fractions from each other after the centrifuge stops spinning for easier and more complete measurement, collection or other post separation processing.

In one embodiment the centrifuge is configured so that the vessel is oriented upright during centrifugation. In such an embodiment the barrier could be generally vertical with the face and side opposite the face being tapered slightly from vertical. Preferably, the face tapers so that the barrier has a greater horizontal width where spaced from the lip than the horizontal width at the lip. This taper can be flat or concave, or other shapes to optimize separation.

In a second embodiment, the centrifuge is configured to support the vessel at an angle away from vertical at least somewhat with upper portions of the vessel closer to the spin axis than lower portions of the vessel. In such a centrifuge, the barrier has a face which is tapered at an angle which causes the tip of the barrier to be further from the spin axis than portions of the face spaced from the tip. With such a configuration, higher density fractions of the sample can over time migrate up the face of the barrier, over the lip and into the catch basin. Similarly, lower density fractions which might begin within the higher density region of the centrifuge can migrate up over the lip of the barrier and into the lower density region of the centrifuge, provided that the density of the particulate fraction is less than the density of the suspending fluid.

For certain separations where higher density fractions are present in relatively small overall percentages of the sample, the higher density region on the higher density side of the barrier benefits from being configured to have a small volume similar to but slightly more than an expected percentage for the higher density fraction of the sample. In this way, a relatively small higher density fraction fills a majority or at least a relatively large minority of the higher density region of the vessel. The higher density fractions of the specimen can then be relatively easily distinguished from the higher density region after spinning of the centrifuge has ceased.

The vessel can be configured with inlet and outlet tubes which access regions on opposite sides of the barrier. These tubes are utilized for introduction of the sample into the vessel and for removal of higher and lower density fractions from the vessel after centrifugation.

OBJECTS OF THE INVENTION

Accordingly, a primary object of the present invention is to provide a vessel for use in a centrifuge which keeps differing density fractions of a sample separate after centrifugation.

Another object of the present invention is to provide a centrifugation vessel which facilitates more rapid separation of differing density fractions therein.

Another object of the present invention is to provide a centrifugation vessel which collects at least some differing density fractions of a sample within a defined space to be more readily measured, removed or otherwise analyzed or processed.

Another object of the present invention is to provide a centrifugation vessel which is customized for the separation of a particular sample into expected fractions.

Another object of the present invention is to provide a centrifugation vessel optimized for separation of a biological sample into at least two fractions of differing densities.

Another object of the present invention is to provide a method for separation of a sample into differing density fractions which also keeps the differing density fractions separate after separation.

Another object of the present invention is to provide a method for more rapidly separating a sample into differing density fractions.

Another object of the present invention is to provide a method for separating and collecting a fraction of a sample after centrifugation.

Another object of the present invention is to provide a centrifuge which separates and collects fractions of different densities from a sample.

Another object of the present invention is to provide a method and apparatus for separating particulate containing fluids into at least two differing density fractions without the need for any moving parts, to enhance operational reliability.

Other further objects of the present invention will become apparent from a careful reading of the included drawing figures, the claims and detailed description of the invention.

BRIEF DESCRIPTION OF THE DRAWINGS

FIG. 1 is a full sectional elevation view of a prior art centrifuge and sample tube supported therein and illustrating prior art separation of fractions of the sample.

FIG. 2 is a front elevation full sectional view of that which is shown in FIG. 1 after rotation of the centrifuge has stopped and illustrating how separated fractions transition to a bottom of the tube after centrifugation.

FIG. 3 is a front elevation full sectional view of a centrifuge and centrifuge vessel according to a first embodiment of this invention with a barrier therein for separate collection of differing density fractions.

FIG. 4 is a front elevation full sectional view of an alternative embodiment of that which is shown in FIG. 3 with a barrier exhibiting a concave face rather than a flat face.

FIG. 10 is a perspective exploded parts view of the centrifuge vessel in the form of a tube preferred for certain forms of biological sample separation.

FIG. 11 is a full sectional front elevation view of that which is shown in FIG. 10.

FIG. 12 is a full sectional front elevation view of that which is shown in FIG. 10 with supply and withdrawal tubes removed and illustrating a variation where a higher density fraction collection region is enlarged by featuring a beveled lower end wall.

FIGS. 13-18 are front elevation views of a series of steps associated with separation and collection of various fractions of a biological sample according to a method of this invention, with some of the figures showing the preferred tube in conjunction with a syringe or supply of a sample or removal of fractions from the tube, and some of the views showing the centrifuge operating on the tube for centrifugation of the sample therein.

DESCRIPTION OF THE PREFERRED EMBODIMENT

Figures 13, 14:
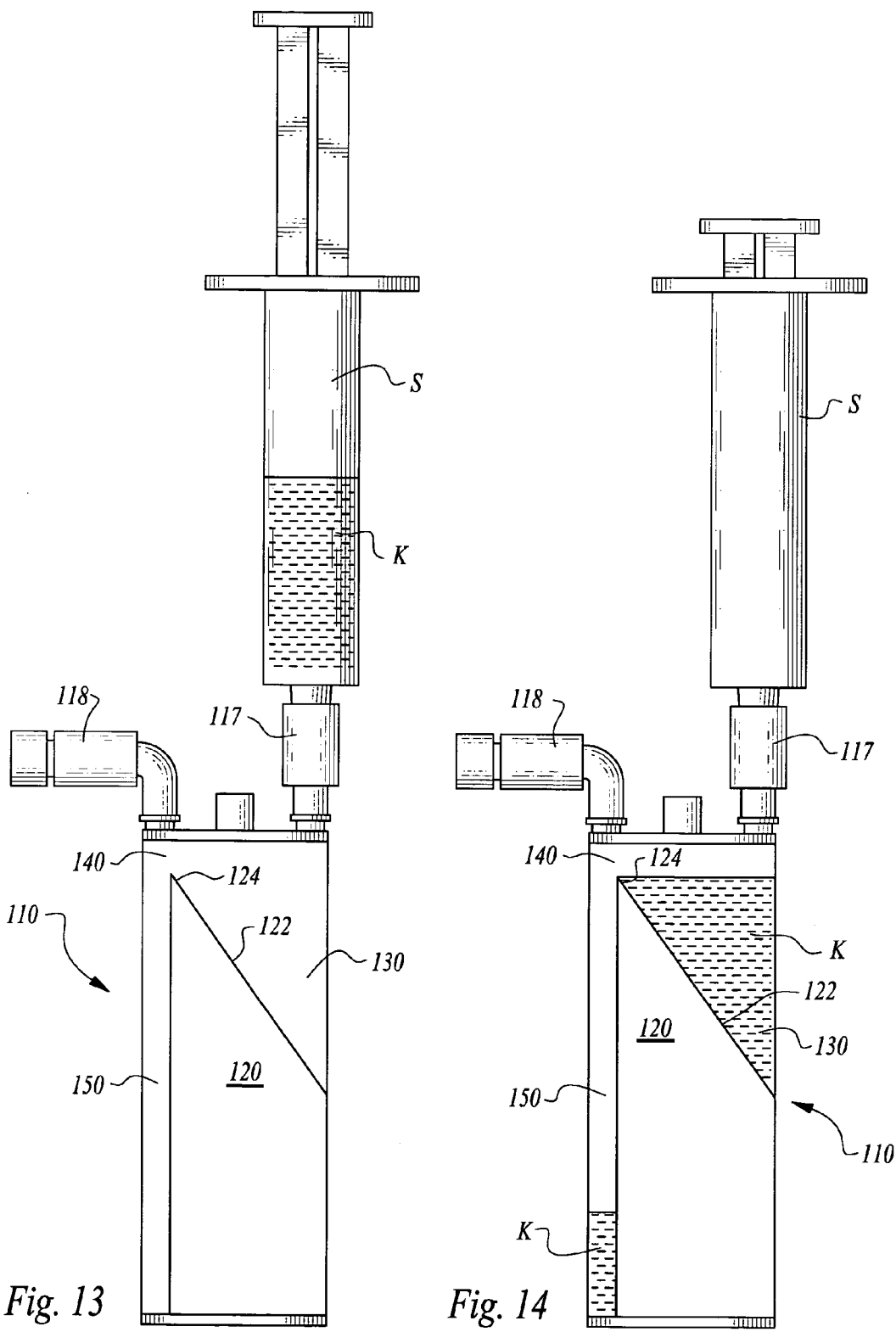

Referring to the drawings, wherein like reference numerals represent like parts throughout the various drawing figures, reference numeral 110 is directed to a preferred tube (FIGS. 10-12) for use in a centrifuge (FIGS. 15 and 16) to separate a sample K (FIGS. 13 and 14) into differing density constituents D, G, E (FIGS. 16-18) for separate collection and removal. By supplying a barrier such as a dam 120 (FIGS. 11 and 12) within a vessel, such as in the form of the tube 110, higher density fractions D of the sample K are caused to migrate through a spillway 140 from a reservoir 130 to a catch basin 150 for separate collection, facilitating later convenient and precise removal of various different fractions of the sample.

In essence, and with particular reference to FIGS. 10-12, basic details of the preferred tube 110 providing a preferred form of centrifugation vessel for biological sample separation, are described. The tube 110 is confined by an outer wall 112 and includes a dam 120 as a preferred form of barrier dividing an interior of the tube 110 into two separate regions. These regions are defined in the preferred embodiment as a reservoir 130 and a catch basin 150. A spillway 140 joins the two regions together over a top of the dam 120. A size of the two regions can be customized to correlate with expected prevalence of differing density fractions within a sample. The dam 120 has a face 122 which is particularly angled to allow migration of higher density fractions up the face 122 and through the spillway 140 into the catch basin 150, and to accelerate such separation. The dam 120 maintains separation even after the centrifuge ceases spinning. The configuration of the dam 120 or other barrier within the tube 110 or other centrifuge vessel can be adjusted for differing types of centrifuges and for use in separation of different samples and to facilitate different rates of separation and degree of completeness of separation.

More specifically, and with particular reference to FIGS. 1 and 2, basic details of prior art centrifuges to which this invention is an improvement, are described. A most basic prior art centrifuge includes a vertical spin axis A with a cradle C configured to support a tube T in an upright fashion extending vertically up out of the cradle C. The sample within the tube T initially fills the tube T up to an initial fluid line B (FIG. 1). When the centrifuge begins to spin (about the spin axis A) a centrifugal force H (FIG. 1) acts laterally upon the sample within the tube T.

Through the effects of higher gee forces upon the sample, higher density fractions of the sample migrate further from the spin axis A leaving lower density fractions of the sample closer to the spin axis A. Such higher density fractions D are illustrated by darker shading relative to lower density fractions E depicted by lighter shading. A boundary F is located between the higher density fraction D and the lower density fraction E with this boundary F defining a transition between these two densities of fluids. A certain amount of time is involved depending on the speed at which the centrifuge rotor rotates and the distance that the cradle C is located away from the spin axis A, and a differential in the densities of the fractions being separated (and other fluid characteristics). Depending on the purposes of the separation, it may be sufficient to only partially separate the sample into differing density fractions, or a greater degree of completeness of separation may be pursued, such as by operating the centrifuge for a longer period of time or changing the geometry of the centrifuge.

One problem with prior art centrifugation using angular and vertical rotors is illustrated in FIG. 2. To measure, remove or otherwise act on fractions of the sample, the centrifuge is typically stopped from spinning. This causes the higher density fraction D to migrate to a bottom of the tube T with the lower density fraction E migrating to an upper portion of the tube T. Such migration takes place over a period of time as the centrifuge slows to a stop. Depending on the nature of the fluid and the difference in the densities between the fluid, and the speed and smoothness with which the centrifuge decelerates to a standstill, some degree of remixing of the fractions tends to occur, such that the boundary is less clearly defined. Measuring, separation and other action on different fractions of the sample is thus made more complex. With such complexity, a greater amount of skill is required for action on different fractions of the sample.

With particular reference to FIG. 3, basic details of a basic tube 10 according to a first embodiment of this invention is described. In this embodiment, the tube 10 acts as a form of centrifuge vessel which resides within the cradle C of the centrifuge vertically similar to the prior art (FIGS. 1 and 2). Uniquely, the tube 10 includes a dam 20 which acts as a barrier extending up from a floor 14 of the tube 10. This dam 20 is typically fixed within the tube 10. An outer wall 12 of the tube 10 defines an interior space of the tube 10 which is divided by the dam 20 into two regions. These regions are referred to as a reservoir 30 and a catch basin 50. Portions of the interior space of the tube 10 above the dam 20 are referred to as a spillway 40 where the two regions come together. A stopper 16 is typically provided to contain the sample within the tube 10 during centrifugation.

The dam 20 can have a variety of different configurations. In a simplest configuration, the dam 20 could merely be a generally vertical wall of nearly constant thickness extending up from the floor 14. Most preferably, the dam 20 includes a face 22 which tapers at an angle down from a lip 24 adjacent the spillway 40, the lip 24 defining a portion of the dam 20 most distant from the floor 14. By angling the face 22, separation is enabled and a rate at which separation occurs can be accelerated. Also, a relative volume of the two regions is adjusted.

In this embodiment, the catch basin 50 has a constant width away from a higher gee side of the tube 10. This width of the catch basin 50 is configured to be small when a higher density fraction D makes up a small portion of the overall sample, and this catch basin 50 can be provided with a greater width and hence a greater volume if the higher density fraction D has a greater proportion of the overall sample. Such matching of the width of the catch basin 50 and the position of the dam 20 or other barrier within the tube 10 can be precise or merely approximate, to meet the design objectives of the user.

Initially, the sample resides within the reservoir 30, and optionally partially within the catch basin 50. During centrifugation, this sample migrates against the higher gee portion (that portion most distant from the spin axis of the centrifuge when the tube 10 is within the spinning centrifuge 2, and the corresponding opposite side being referred to as the "lower gee side") of the outer wall 12 of the tube 10, such that the catch basin 50 is filled with fluid and the reservoir 30 is only partially filled, with fluid extending over the dam 20 and within the spillway 40 region. The dam 20 can vary in height. In some instances where a small initial sample is being separated, the dam 20 might extend as little as five percent of the way from the floor of the tube 10 up to a top of the tube 10. In other embodiments, the dam 20 might extend up to ninety-nine percent of a height of the tube 10.

As separation occurs, a surface of the sample is defined by line J (FIG. 3) with a boundary between fractions of differing density is established as line I (FIG. 3). Then, when the centrifuge ceases operation, and slows to a stop, the higher density fluid D remains within the catch basin 50 and the lower density fraction E falls down into the reservoir E. The separation of the differing density fluids is thus maintained even after the centrifuge has stopped rotating. This is in contrast to the less precise boundary F (FIG. 2) provided by the prior art. Furthermore, collection can be made more precise, and less complex in that collection of higher density fluid D merely involves extraction from the catch basin 50.

In FIG. 4, an alternative to the tube 10 of FIG. 3 is depicted, in the form of tube 60. This alternative tube 60 includes an outer wall 62 extending up from a floor 64 and with the alternative tube 60 closed by a stopper 66. Such details are similar to those of the tube 10 (FIG. 3). In this embodiment, an alternative dam 70 is provided which uniquely exhibits a concave face 72 which has a concave curving taper from the floor 64 up to a lip 74, defining an uppermost portion of the alternative dam 70. The alternative dam 70 divides a reservoir 80 from a catch basin 100 with a spillway 90 joining reservoir 80 and catch basin 100 together.

Operation of the alternative tube 60 within a centrifuge occurs similar to the operation described above with respect to the tube 10 (FIG. 3). However, because the alternative dam 70 has a concave face 72, separation of the higher density fraction can occur more rapidly. In particular, note that as the face 72 transitions towards the tip 74, a steeper angle is presented by the face 72, so that a greater and greater force is required to cause the higher density fraction to migrate over the tip 74 and into the catch basin 100. However, as the higher density fraction D moves closer to the higher gee wall of the tube 60, greater and greater forces are acting on the higher density fluid D to drive the higher density fluid D over the tip 74. With such a concave contour for the face 72, these characteristics are optimized for rapid separation.

Figure 5:
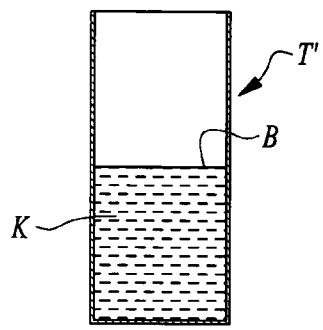
FIGS. 5-9 are full sectional front elevation views of a prior art tube undergoing centrifugation in a centrifuge having a cradle which is angled to cause upper portions of the tube to be closer to a spin axis of the centrifuge than lower portions of the tube, and illustrating separation of differing density fractions according to the prior art for such centrifuges.
Figure 6:
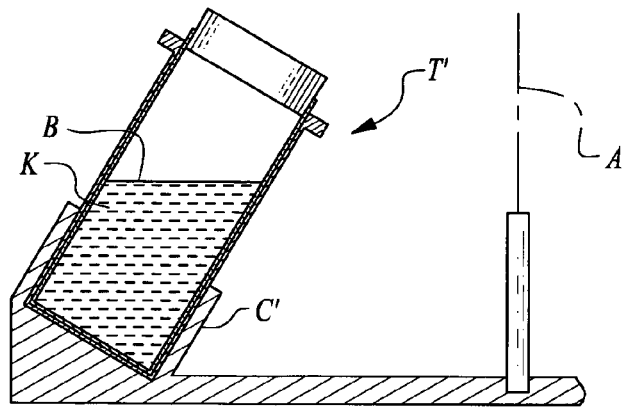
Figure 7:
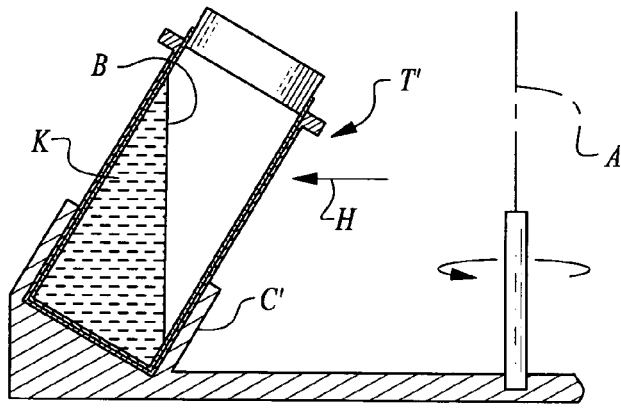
Figure 8:
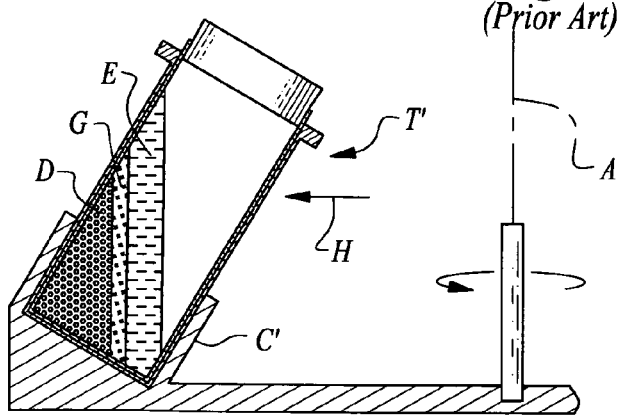

With particular reference to FIGS. 5-9, details of a prior art tube T' for use in a cradle C' of a centrifuge exhibiting an angled cradle C' are described. In this prior art centrifuge, the cradle C' is angled (FIG. 6) so that the upper end of the tube T' is closer to the spin axis A at a lower portion of the tube T' which resides within the cradle C'. An initial fluid line B for a sample K remains horizontal before spinning of the centrifuge, with such horizontal fluid line B parallel with the floor before placement in the centrifuge and then angled relative to the floor and non-perpendicular to outer walls of the tube T' after placement within the cradle C' (FIGS. 5 and 6).

When the centrifuge begins to spin (about spin axis A (FIG. 7)) centrifugal forces acting along arrow H (FIG. 7) cause this initial fluid line B to be angled to approximately vertical. Centrifuges are allowed to continue to spin at a sufficiently high rate to cause the higher density fraction D to migrate further from the spin axis A, displacing a lower density fraction E toward the spin axis A. In the representation depicted in FIG. 8, a mid-density fraction G is also separated which migrates to a location between the higher density fraction D and the lower density fraction E. One such sample K is a biological sample which includes higher density fractions D in the form of "pellet" material and lower density fluid E in the form of plasma and mid-density fluid G is in the form of a "buffy coat."

Figure 9:
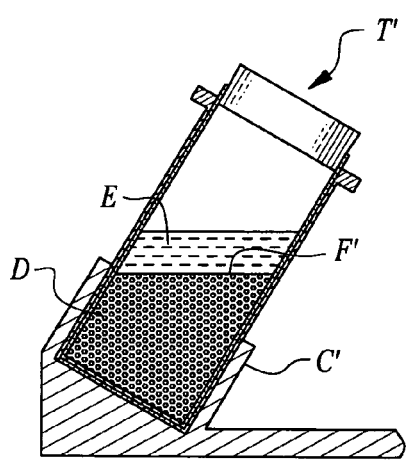

Once separation is complete, the centrifuge is decelerated to a stop so that the final position of the fluids within the tube T' are similar to that depicted in FIG. 9. Note that depending on the characteristics of the biological sample, it can be difficult to maintain full separation. As the various density fractions migrate from their position during centrifugation (FIG. 8) and after stopping of the centrifuge (FIG. 9) an opportunity is presented for remixing of the various different fractions to some extent. As depicted in FIG. 9, a boundary F' can tend to absorb into the mid-density fraction G making this mid-density fraction G difficult to identify, measure or extract.

Even if the separation remains complete, if the mid-density fluid is a relatively small proportion of the overall sample, extraction can be rather difficult in that an extraction tube must be carefully placed at a depth precisely within such a mid-layer without being too deep or too shallow. Such procedures typically require skilled personnel and are not highly amenable to automation and high reliability processing, unless exceptional care is taken to ensure that the proper fraction is being extracted from the tube T'.

With particular reference to FIGS. 10-12, details of a preferred tube 110 for use in separating fractions from a sample K such as a biological sample are described. This tube 110 provides the preferred form of centrifuge vessel for certain forms of separations. Variations on this preferred tube 110 can be made to accommodate samples having different fraction constituent percentages, or for separations which have fractions which have a greater or lesser density differential from each other, or for separations which are optimized for completeness of separation or optimized for speed, or optimized for simplicity of the centrifuge vessel, or optimized for other parameters defined by the user.

With this preferred tube 110, an outer wall 112 defines an interior space of the tube 110. This outer wall 112 is preferably cylindrical with a circular cross-section, but could have other contours. The outer wall 112 extends up from a floor 114 to an upper end which is enclosed by a cap 116. With this preferred tube 110, access into an interior of the tube 110 occurs through the cap 116. In particular, an in port 117 is supplied for accessing one side of an interior of the tube 110 and an out port 118 is provided for accessing of an opposite side of an interior of the tube 110. An air port 119 is optionally provided to allow for removal of air or other fluids contained within the tube 110 during introduction of a sample to be separated. If required, a check valve or other filter 115, such as an anti-microbial filter can be associated with the air port 119 to prevent leakage or contamination from the air port 119 during centrifugation. As an alternative, the tube 110 could be initially filled with a vacuum, so that no such air port 119 would be required. As another alternative, air could be removed through one of the ports 117, 118 while a sample is introduced into the tube 110 through the other of the ports 118, 117.

The tube 110 includes a barrier therein which separates an interior of the tube 110 into two regions including a lower gee region located closer to a spin axis A (FIG. 16) of the centrifuge and a higher gee region located further from the spin axis A of the centrifuge. This barrier is preferably in the form of a dam 120 with the two regions defined as a reservoir 130 closer to the spin axis A (FIG. 16) and a catch basin 150 on a side of the dam 120 further from the spin axis A. A spillway 140 joins the reservoir 130 and catch basin 150 together over the dam 120.

The dam 120 could conceivably be a planar structure of constant thickness. With such a configuration, the dam 120 would be angled at an angle matching an angle of the cradle C' (FIGS. 15 and 16) so that this dam 120 would have approximately vertical sides when undergoing centrifugation.

Most preferably, the dam 120 has a non-uniform width with a narrowest portion of the dam 120 at a lip 124 adjacent the spillway 140 and most distant from the floor 114. This dam 120 has a face 122 facing the reservoir 130 which tapers non-parallel to the inner surface of the outer wall 112 and non-perpendicular to the floor 114. The taper can be flat as depicted in FIGS. 11 and 12, or can be concave (similar to FIG. 4) or exhibit other contours.

The angle of the face 122 is selected so that the lip 124 of the dam 120 is further from the spin axis A than any other portions of the face 122. This angle of the face 122 away from vertical measures greater than zero degrees and the tube 110 has operated successfully with the face 122 angle being five degrees. While a range from one to ten degrees is considered optimal, face 122 angles up to about thirty degrees may be effective in some cases. With such a configuration, higher density fractions within a sample can migrate up along the face 122 up to the lip 124, through the spillway 140 and into the catch basin 150. As can be seen, if the face 122 tapered so that the lip 124 was closer to the spin axis A than other portions of the base 122, higher density fractions would become trapped within the reservoir 130 and full separation would be frustrated.

A surface of the dam 120 opposite the face 122 benefits in this embodiment from being substantially parallel with the outer wall 112. Furthermore, the catch basin 150 is preferably rather thin so that the catch basin 150 has a smaller volume than the reservoir 130. Such smaller volume is particularly beneficial when the sample being separated has a higher density fraction D (FIG. 6) which makes up a smaller proportion of the sample K (FIG. 14) than the lower density fraction E.

The reservoir 130 includes a supply tube 132 extending thereinto through the cap 116. The supply tube 132 extends down to a tip 133 from which fluids can be directed into the reservoir 130. A plug 134 is provided for plugging the supply tube 132 outside of the cap 116, such as to prevent discharge of fluids during centrifugation. While the supply tube 132 is coupled to the in port 117 in the cap 116, the supply tube 132 could be used for both introduction and removal of fluids from within the tube 110.

In one embodiment a withdrawal tube can be configured to include a curving lower tip so that it withdraws a fraction primarily from above a bottom end of the tip. If the tip faces down, a false floor deflection plate can be fitted on the catch basin so that withdrawal of constituents above such a false floor does not capture constituents below the false floor. Such a withdrawal tube can be particularly effective in extracting a medium density constituent, such as a "buff coat," platelet rich plasma or a stromal vascular fraction from adipose tissue.

The catch basin 150 includes the withdrawal tube 152 extending down from the cap 116 and in communication with the out port 118. The withdrawal tube 152 extends down to a tip 153. This tip 153 is preferably in a lower half of the catch basin 150 and most preferably directly adjacent to the floor 114, with only sufficient space to prevent blocking of the tip 153. A plug 154 can be provided for closing off the out port 118, such as to prevent leakage from the tube 110 during centrifugation. While the withdrawal tube 152 and out port 118 are primarily used for removal of fractions after centrifugation, these structures could similarly be utilized for introduction of fluids into the tube 110.

The catch basin 150 benefits from having a constant width and dimensions which make it significantly elongated with a height many times greater than its width. In this manner, a relatively small higher density fraction D (FIGS. 16 and 17) can be more easily discerned and measured. Furthermore, the precise positioning of a tip 153 of a withdrawal tube 152 within a fraction to be removed can more effectively occur when the catch basin 150 has such an elongate geometry.

In one embodiment, where it is desirable that the catch basin 150 to have a larger volume, a lower end of the catch basin 150 is provided with a beveled lower end wall 155 (FIG. 12). In such an embodiment, a relatively narrow upper portion of the catch basin 150 can still be provided for precise measurement and collection of mid-density fractions G when the sample has a relatively large amount of higher density fraction D and lower density fraction E, by locating the mid-density fraction G within the narrower upper portion of the catch basin 150. With such a beveled lower end wall 155, an angle of this beveled lower end wall is carefully selected so that lower portions of this end wall adjacent the floor 114 are further from the spin axis A than upper portions of this beveled lower end wall 155. In such a way, any lower density fraction E beginning within a bottom of the catch basin 150 can migrate up to the catch basin 150 and over the spillway 140 into the reservoir 130 during centrifugation, rather than trapping lower density fractions within the catch basin 150.

With particular reference to FIGS. 13-18, details of a method of separating a sample A into differing density fractions, and particularly a biological sample having a higher density fraction "pellet" D, a lower density fraction E and a mid-density "buffy coat" fraction G are described. This method is utilized for the preferred tube 110 in a most preferred form of this method, but could similarly operate with other tubes 110. Initially, a syringe S or other source of sample K is coupled to the in port 117 and the sample K is inputted into the reservoir 130. The sample K can be sufficiently large that some portions of the sample K also initially migrate into the catch basin 150.

Figure 16:
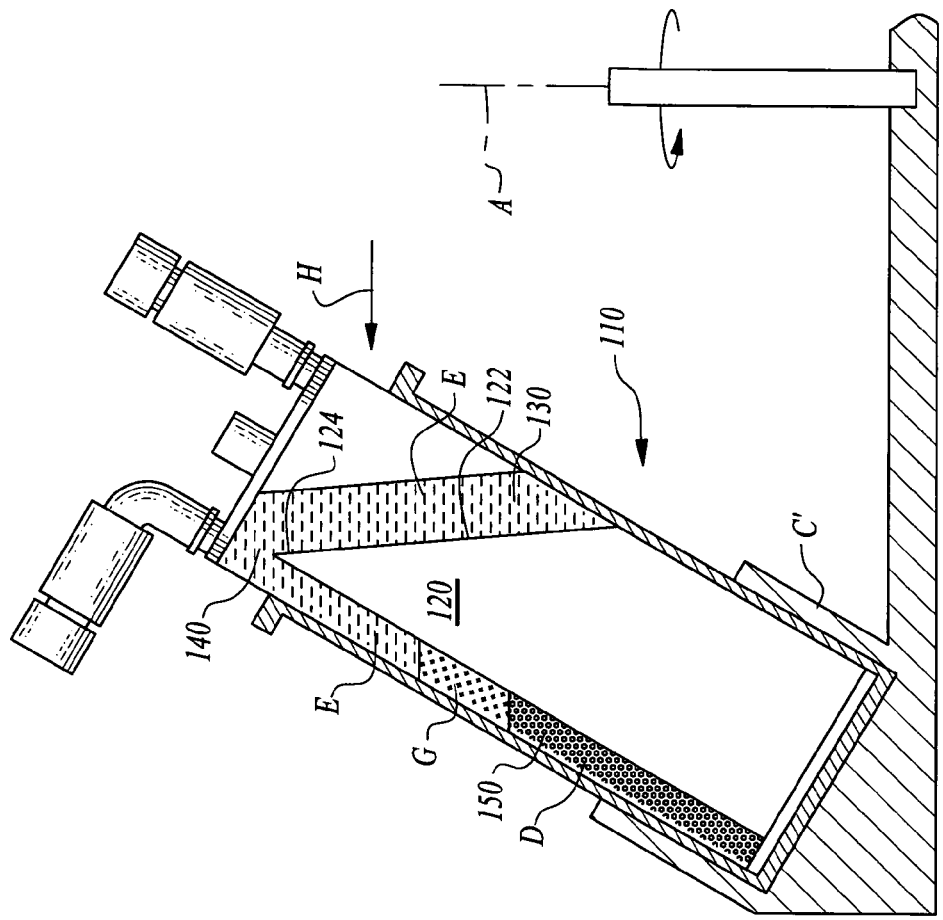
Figure 15:
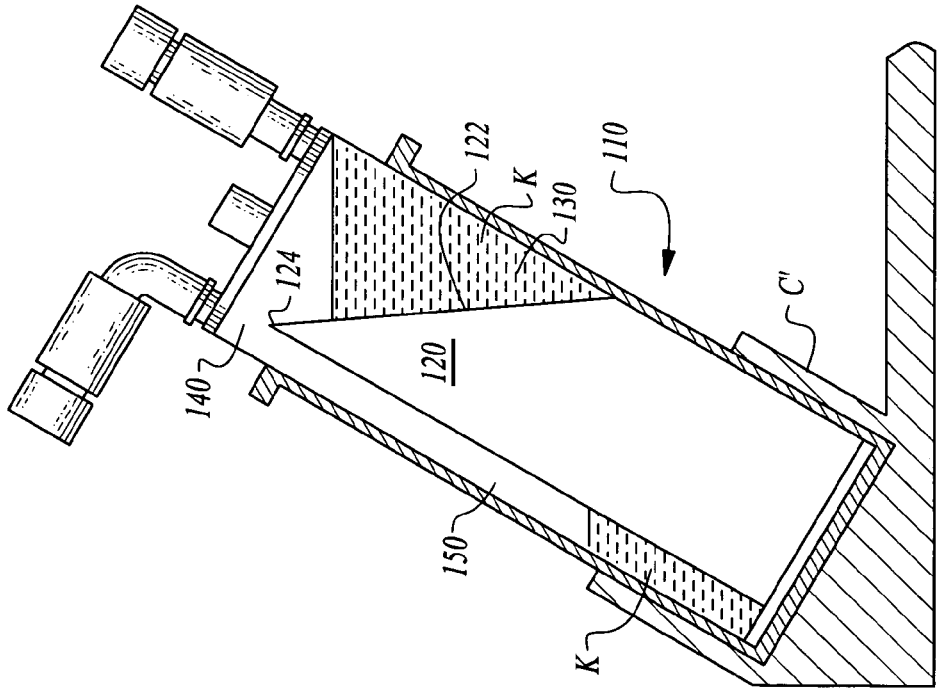

The tube 110 is then placed within the cradle C' of a centrifuge. Plugs 134, 154 are placed within the in port 117 and out port 118 to keep the sample K contained within the tube 110 (FIG. 15). The centrifuge is then caused to spin about the spin axis A (FIG. 16). Initially, the sample K is still homogenous and migrates to completely fill the catch basin 150 and only partially fill the reservoir 130. Because the taper of the face 122 is such that the lip 124 on the dam 120 is further from the spin axis A then other portions of the face 122, higher density fraction D portions of the sample K migrate up the face 122, over the lip 124, through the spillway 140 and into the catch basin 150. Similarly, lower density fractions E that originally start within the catch basin 150 can migrate up out of the catch basin 150 and over the lip 124 of the dam 120, through the spillway 140 and into the reservoir 130.

Such centrifugation continues until separation has been completed to the satisfaction of the user, and the higher density fraction D is located within the lower portion of the catch basin 150, with lower density fraction E fluid contained within the reservoir 130, and possibly upper portions of the catch basin 150. A mid-density fraction G, such as a buffy coat, resides in a mid-portion of the spillway 140. Due to a thinness of the catch basin 150 and elongate form, the buffy coat G which makes up a small percentage of the overall sample K takes up a visually significant readily discernible portion of the catch basin 150 for ready measurement and collection therefrom.

In particular, the tube 110 is removed and placed upright (FIG. 17). The various different fractions of the sample remain separated by the dam 120. The plug 154 on the out port 118 is removed and the syringe S coupled to the out port 118. Because the withdrawal tube 152 in this embodiment extends down to a bottom of the catch basin 150, the syringe is used to first extract the higher density "pellet" portion of the biological sample. This causes the mid-density fraction G "buffy coat" to migrate down to a bottom of the catch basin 150 and portions of the lower density fraction E to also migrate down somewhat within the catch basin 150. Once all of the higher density fluid D has been removed, the syringe S can be decoupled from the outport 118 for discharge of the higher density fraction D from the syringe S for separate collection and potential use. The syringe S is then re-coupled to the outport 118 and further extraction through the withdrawal tube 152 causes collection of the mid-density fraction G "buffy coat" of the biological sample for collection and use.

Figure 19:
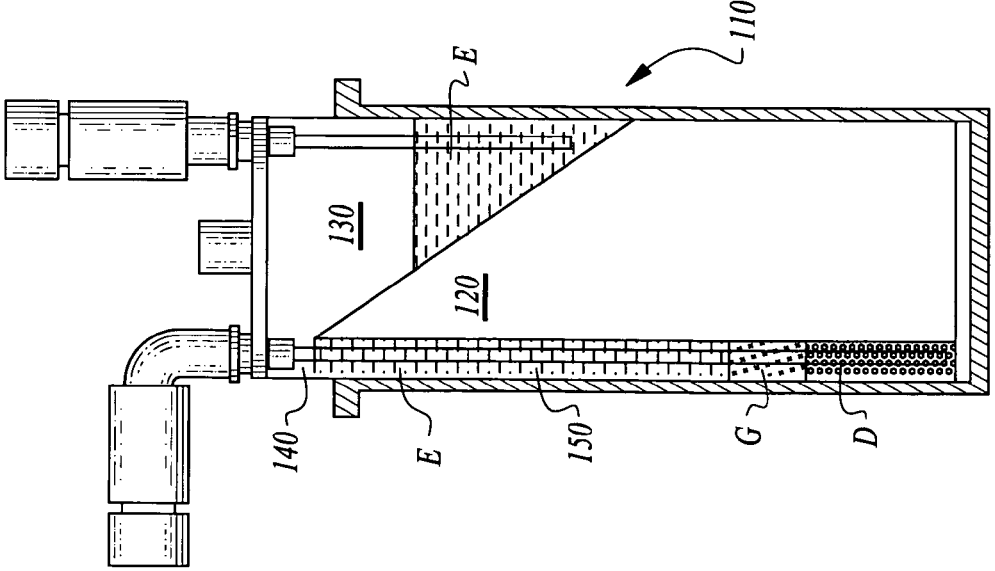
FIGS. 19-21 are front elevation full sectional views of the tube of FIG. 10 and illustrating how different biological samples can locate differing density fractions thereof in different locations depending on the characteristics of the sample, such as the hematocrit level of a blood sample.
Figure 20:
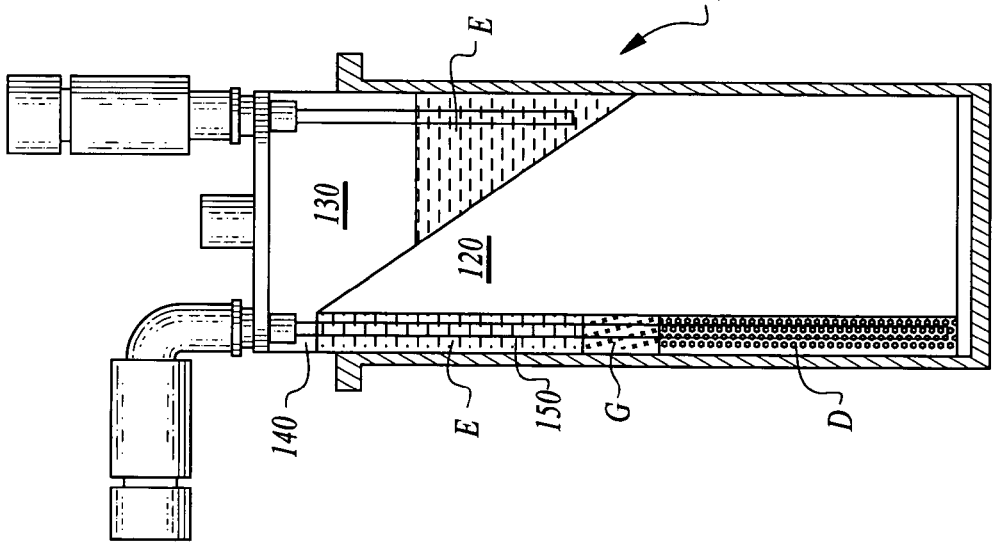
Figure 21:
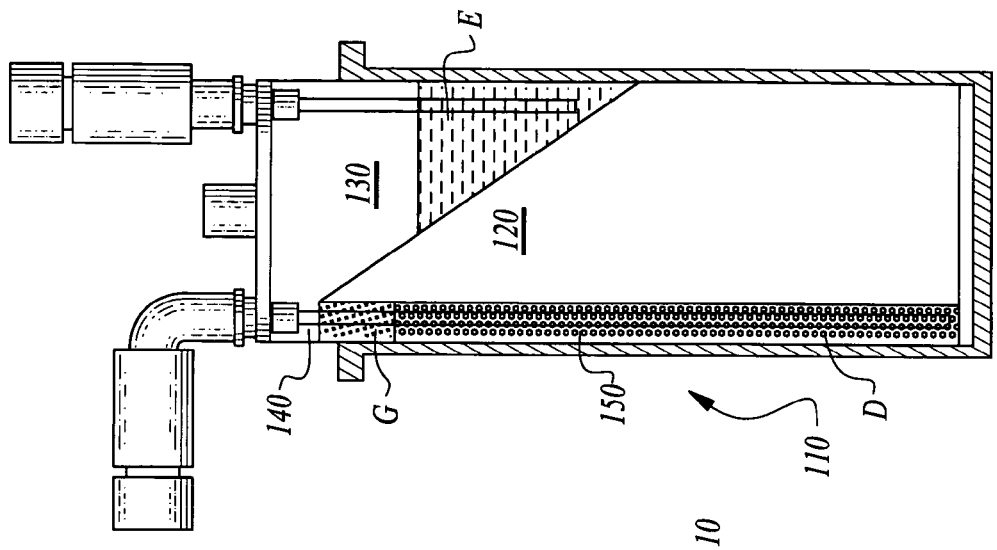

With such a methodology, samples having somewhat differing prevalence of differing density fractions can be accommodated without requiring the withdrawal tube 152 to have a precise length which would only be suitable for certain blood characteristics. For instance, with changes in hematocrit levels, a greater or lesser degree of higher density fraction D "pellet" portions of the biological sample K are present. With the tube 110 configured as depicted in FIGS. 19-21, the buffy coat G remains within the catch basin 150 for all biological sample hematocrit levels. By having the withdrawal tube 152 extend down to the floor 114, the higher density fraction D is always first removed, followed by the mid-density fraction buffy coat G. In such a manner, similar collection protocols can be utilized for samples having differing characteristics and reliable separation and collection is achieved.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A centrifuge and fluid containing vessel, comprising in combination:
   a spin axis;
   a centrifuge vessel adapted to contain a fluid within an outer wall thereof;
   at least one cradle adapted to support said centrifuge vessel, said cradle spaced from said spin axis;
   said cradle adapted to spin about said spin axis, wherein said cradle has an upper end which is open and into which said centrifuge vessel is adapted to be removably placed along a cradle center line, said center line of said cradle oriented substantially parallel with said spin axis;
   said centrifuge vessel having said outer wall surrounding a fluid containing interior space of said vessel; and
   said vessel including a barrier inside said outer wall, said barrier partially dividing said interior space into two regions and said barrier having a lip, with said two regions connected above said lip and said two regions spaced apart below said lip, wherein said barrier includes a face extending down from said lip on a side of said barrier closest to said spin axis, said face extending at an angle tapering toward said spin axis as said face extends away from said lip.

2. The combination of claim 1 wherein said face tapers in a curving manner away from said lip and partially toward said spin axis as said face extends away from said lip.

3. A centrifuge and fluid containing vessel, comprising in combination:
   a spin axis;
   a centrifuge vessel adapted to contain a fluid within an outer wall thereof;
   at least one cradle adapted to support said centrifuge vessel, said cradle spaced from said spin axis;
   said cradle adapted to spin about said spin axis, wherein said cradle includes an open upper end into which said centrifuge vessel is adapted to be removably placed along a center line of said cradle, said center line of said cradle angled non-parallel to said spin axis with said open upper end of said cradle located closer to said spin axis than other portions of said cradle;
   said centrifuge vessel having said outer wall surrounding a fluid containing interior space of said vessel; and
   said vessel including a barrier inside said outer wall, said barrier partially dividing said interior space into two regions and said barrier having a lip, with said two regions connected above said lip and said two regions spaced apart below said lip.

4. The combination of claim 3 wherein said barrier has a face extending down from said lip on a side of said barrier closest to said spin axis, said face angled to be closer to said spin axis where said face is spaced from said lip than a distance from said face to said spin axis where said face is adjacent said lip.

5. The combination of claim 4 wherein a side of said barrier opposite said face is oriented substantially parallel with portions of said outer wall most distant from said spin axis for at least a portion of said barrier.

6. The combination of claim 5 wherein portions of a side of said barrier opposite said face taper at an angle relative to portions of said outer wall of said vessel most distant from said spin axis, said angle causing tapering portions of said wall of said barrier opposite said face to be most distant from said spin axis at a location most distant from said lip of said barrier.

* * * * *